United States Patent
Schreiber

(10) Patent No.: US 9,982,057 B2
(45) Date of Patent: May 29, 2018

(54) HUMAN TNFRSF25 ANTIBODY

(71) Applicant: Pelican Therapeutics, Inc., Durham, NC (US)

(72) Inventor: Taylor H. Schreiber, Durham, NC (US)

(73) Assignee: PELICAN THERAPEUTICS, INC., Durham, NC (US)

( * ) Notice: Subject to any disclaimer, the term of this patent is extended or adjusted under 35 U.S.C. 154(b) by 0 days. days.

(21) Appl. No.: 15/527,430

(22) PCT Filed: Nov. 17, 2015

(86) PCT No.: PCT/US2015/061082
§ 371 (c)(1),
(2) Date: May 17, 2017

(87) PCT Pub. No.: WO2016/081455
PCT Pub. Date: May 26, 2016

(65) Prior Publication Data
US 2017/0362329 A1    Dec. 21, 2017

Related U.S. Application Data

(60) Provisional application No. 62/134,740, filed on Mar. 18, 2015, provisional application No. 62/080,694, filed on Nov. 17, 2014.

(51) Int. Cl.
*C07K 16/28* (2006.01)
*A61K 39/395* (2006.01)

(52) U.S. Cl.
CPC ........ *C07K 16/2878* (2013.01); *A61K 39/395* (2013.01); *C07K 2317/24* (2013.01); *C07K 2317/51* (2013.01); *C07K 2317/515* (2013.01); *C07K 2317/565* (2013.01); *C07K 2317/567* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 4,935,496 A | 6/1990 | Kudo et al. |
| 5,502,167 A | 3/1996 | Waldmann et al. |
| 5,530,101 A | 6/1996 | Queen et al. |
| 5,558,864 A | 9/1996 | Bendig |
| 5,565,332 A | 10/1996 | Hoogenboom et al. |
| 5,585,089 A | 12/1996 | Queen et al. |
| 5,639,641 A | 6/1997 | Pedersen et al. |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,705,154 A | 1/1998 | Dalie et al. |
| 5,733,743 A | 3/1998 | Johnson et al. |
| 5,750,078 A | 5/1998 | Shitara et al. |
| 5,770,403 A | 6/1998 | Dalie et al. |
| 9,017,679 B2 | 4/2015 | Podack et al. |
| 9,499,627 B2 | 11/2016 | Podack et al. |
| 9,603,925 B2 | 3/2017 | Podack et al. |
| 2007/0104715 A1 | 5/2007 | Nordstedt et al. |
| 2007/0128184 A1 | 6/2007 | Podack et al. |
| 2008/0003221 A1 | 1/2008 | Podack et al. |
| 2009/0324600 A1 | 12/2009 | Haeuw et al. |
| 2010/0092470 A1 | 4/2010 | Bhatt et al. |
| 2011/0243951 A1 | 10/2011 | Podack et al. |
| 2012/0014950 A1 | 1/2012 | Migone et al. |
| 2012/0328559 A1 | 12/2012 | Podack et al. |
| 2013/0251729 A1 | 9/2013 | Kuhne et al. |
| 2013/0281922 A1 | 10/2013 | Teipe |
| 2014/0193410 A1 | 7/2014 | Podack et al. |
| 2014/0286950 A1 | 9/2014 | Diehl et al. |
| 2016/0015779 A1 | 1/2016 | Podack et al. |
| 2017/0226218 A1 | 8/2017 | Podack et al. |

FOREIGN PATENT DOCUMENTS

WO    WO 2016/081455    5/2016

OTHER PUBLICATIONS

U.S. Appl. No. 15/618,993, filed Jun. 9, 2017, Poddack et al.
Baldrick, "Toxicokinetics in prechnical evaluation." *Regul Toxicol Pharmacol* 32:210-218, 2000.
Bodmer et al., "TRAMP, a novel apoptosis-mediating receptor with sequence homology to Tumor Necrosis Factor Receptor 1 and FAS (Apo-1/CD95)," *Immunity* 6(1):79-88, 1997.
Bu et al., "Expression and function of TNF-family proteins and receptors in human osteoblasts," *Bone* 33(5):760-770, 2003.
Charman, "Lipids, lipophilic drugs, and oral drug delivery—some emerging concepts,"*J Pharm Sci* 89:967-978, 2000.
Cole et al., "The EBV-hybridoma technique and its application to human lung cancer," in *Monoclonal Antibodies and Cancer Therapy*, Alan R. Liss, Inc., 77-96, 1983.
Cote et al., "Generation of human monoclonal antibodies reactive with cellular antigens," *Proc Natl Acad SCi USA* 80:2026, 1983.
Huse et al., "Generation of a large combinatorial library of the immunoglobulin repertoire in phage lambda," *Science*, 246: 1275, 1989.
International Preliminary Report on Patentability in International Application No. PCT/US2015/061082, dated May 23, 2017, 8 pages.
International Search Report and Written Opinion in International Application No. PCT/US15/061082 dated Mar. 11, 2016, 8 pages.
Jones et al., " Replacing the complementarity-determining regions in a human antibody with those from a mouse," *Nature* 321:522, 1986.
Kitson et al., "A death-domain-containing receptor that mediates apoptosis," *Nature* 384(6607):372-375,1996.
Kohler et al., "Continuous cultures of fused cells secreting antibody of predefined specificity," *Nature* 256:495, 1975.

(Continued)

*Primary Examiner* — Daniel C Gamett
(74) *Attorney, Agent, or Firm* — Morgan, Lewis & Bockius LLP, BO

(57) ABSTRACT

Antibodies and antigen binding fragments that bind specifically to TNFRSF25 are provided herein. Methods for using the antibodies and antigen binding fragments to, for example, stimulate proliferation of human T cells (e.g., CD8+ T cells) and to treat cancer patients also are provided.

10 Claims, 10 Drawing Sheets

(56) References Cited

OTHER PUBLICATIONS

Konieczny et al., "The combination of IgM subunits and proteolytic IgG fragments by controlled formation of interchain disulphides," *Haematologia* (Budap.) 14:95, 1981.

Kozbor and Roder, "The production of monoclonal antibodies from human lymphocytes," *Immunology Today* 4:72, 1983.

Kunkel, "Rapid and efficient site-specific mutagenesis without phenotypic selection," *Proc Natl Acad Sci USA* 82(2):488-492, 1985.

Morrison et al., "Chimeric human antibody molecules: mouse antigen-binding domains with human constant region domains," *Proc Natl Acad Sci USA* 81:6851-6855, 1984.

Powell et al., "Compendium of excipients for parenteral formulations," *PDA J Pharm Sci Technol* 52:238-311, 1998.

Reddy et al., "TNFRSF25 agonistic antibody and Galectin-9 combination therapy controls herpes simplex virus-induced immunoinflammatory lesions," *J Virol* 86(19):10606-10620, 2012.

Riechmann et al., "Reshaping human antibodies for therapy," *Nature* 332:323, 1988.

Schreiber et al., "Therapeutic Treg expansion in mice by TNFRSF25 prevents allergic lung inflammation," *J Clin Invest* 120(10):3629-3640, 2010.

Schreiber et al., "T cell costimulation by TNFRSF4 and TNFRSF25 in the context of vaccination," *J Immunol* 189(7):3311-3318, 2010.

*Short Protocols in Molecular Biology*, Chapter 11, Green Publishing Associates and John Wiley & Sons, Ed. Ausubel et al., 1992.

Wang, "Lyophilization and development of solid protein pharmaceuticals," *Int J Pharm* 203:1-60, 2000.

Wolf et al., "Tregs expanded in vivo by TNFRSF25 agonists promote cardiac allograft survival,"*Transplantation* 94(6)569-574, 2012.

| | FR1 | CDR1 | FR2 | CDR2 |
|---|---|---|---|---|
| Hamster-VH | EVQLVESGGGLSQPGNSLQLSCEAS | GFTFSNHDLN | WVRQAPGKGLEWVAY | ISSSASGLISYADAVRG |
| IGHV3-7*03 | V G R A | | A | |
| IGHV3-48*03 | V G R A | | S | |
| WBP300-hVH1 | V G R E | | A | |
| WBP330-hVH2 | V G R A | | A | |
| WBP330-hVH3 | V G R E | | S | |
| WBP330-hVH4 | V G R A | | S | |

| | FR3 | CDR3 | FR4 |
|---|---|---|---|
| Hamster-VH | RFTISRDNAKNSLFLQMNNLKSEDTAMYYCAR | DPPYSGLYALDF | WGQGTQVTVSS (SEQ ID NO:1) |
| IGHV3-7*03 | Y S RA V | | |
| IGHV3-48*03 | Y S RA V | | |
| WBP300-hVH1 | Y S RA V | | |
| WBP330-hVH2 | Y S RA V | | |
| WBP330-hVH3 | Y S RA V | | |
| WBP330-hVH4 | Y S RA V | | |

FIG. 4A

| | FR1 | | CDR1 | | FR2 | | CDR2 |
|---|---|---|---|---|---|---|---|
| Hamster-VL | QPVLTQSPSASASLSGSVKLTC | | TLSSELSSYTI | W | YQQRPDKAPKYVMY | H Q G A R L Y | LKSDGSHSKGD |
| IGLV4-60*03 | P | S | GS | | | H Q G A R L Y | |
| IGLV4-69*01 | L | P | GA | | | H Q E G R L K | |
| WBP330-hVL1 | P | S | GS | | | H Q G A R L Y | |
| WPB330-hVL2 | L | P | GA | | | H Q E G R L K | |

| | FR3 | | | CDR3 | FR4 |
|---|---|---|---|---|---|
| Hamster-VL | GIPDRFSGSSSGAHRYLSISNVQSEDDATYFC | V | D T NL | EDYGAGYTLAGQYGW | FGSGTKVTVL (SEQ ID NO:2) |
| IGLV4-60*03 | | I | E T SL | EDY | |
| IGLV4-69*01 | | V | D T NL | EDY | |
| WBP330-hVL1 | | I | E T SL | EDY | |
| WPB330-hVL2 | | | | | |

FIG. 4B

US 9,982,057 B2

HUMAN TNFRSF25 ANTIBODY

CROSS-REFERENCE TO RELATED APPLICATIONS

This application is a National Stage application under 35 U.S.C. § 371 of International Application No. PCT/US2015/061082 having an International Filing Date of Nov. 17, 2015, which claims benefit of priority from U.S. Provisional Application No. 62/134,740, filed on Mar. 18, 2015, and U.S. Provisional Application No. 62/080,694, filed on Nov. 17, 2014, both of which are incorporated herein by reference in their entirety.

TECHNICAL FIELD

This document relates to antibodies and antigen binding fragments thereof that bind specifically to TNFRSF25, and to methods for using the antibody and antigen binding fragments to, for example, stimulate proliferation of human T cells (e.g., CD8+ T cells), and to treat cancer patients.

BACKGROUND

Tumor necrosis factor receptor superfamily member 25 (TNFRSF25) is a member of the TNF-receptor superfamily that is preferentially expressed by activated and antigen-experienced T lymphocytes. TNFRSF25 is activated by the TL1A (TNFSF15) ligand, which is rapidly upregulated in antigen presenting cells and in some endothelial cells following Toll-Like Receptor or Fc receptor activation. TNFRSF25 can stimulate NF-kappa B activity, and also can stimulate caspase activation to regulate cell apoptosis (Bodmer et al., *Immunity* 6(1):79-88, 1997; and Kitson et al., *Nature* 384(6607):372-375, 1996). Alternative splicing produces multiple distinct isoforms of TNFRSF25, most of which are potentially secreted molecules. Alternative splicing of the TNFRSF25 gene in B and T cells encounters a program change upon T-cell activation, which predominantly produces full-length, membrane bound isoforms, and is thought to be involved in controlling lymphocyte proliferation induced by T-cell activation.

Activation of TNFRSF25 is dependent on previous engagement of the T cell receptor. After binding to TL1A, TNFRSF25 signaling increases the sensitivity of T cells to endogenous IL-2, and enhances T cell proliferation. Since activation of TNFRSF25 is T cell receptor dependent, the activity of TNFRSF25 in vivo is specific to T cells that are encountering cognate antigen. At rest, and when there is no underlying autoimmunity, the majority of T cells that regularly encounter cognate antigen are FoxP3+ regulatory T cells. Stimulation of TNFRSF25, in the absence of any other exogenous signals, stimulates highly specific proliferation of FoxP3+ regulatory T cells from a baseline of 8-10% of all CD4+ T cells to 35-40% of all CD4+ T cells, within five days (Schreiber et al., *J Clin Invest* 120(10):3629-3640, 2010). Therapeutic agonists of TNFRSF25 can be used to stimulate Treg expansion, which can reduce inflammation in experimental models of asthma, allogeneic solid organ transplantation, and ocular keratitis (Schreiber et al., supra; Reddy et al., *J Virol* 86(19):10606-10620, 2012; and Wolf et al., *Transplantation* 94(6):569-574, 2012). Similarly, because TNFRSF25 activation is antigen dependent, costimulation of TNFRSF25 together with an autoantigen or with a vaccine antigen can lead to exacerbation of immunopathology or enhanced vaccine-stimulated immunity, respectively (Schreiber et al., *J Immunol* 189(7):3311-3318, 2010).

SUMMARY

This document provides agonistic human and humanized TNFRSF25 specific monoclonal antibodies, and antigen binding fragments thereof. Also provided herein are methods for, inter alia, using the antibodies and antigen binding fragments to stimulate proliferation of human T cells, as well as methods for using the antibodies and antigen binding fragments in the treatment of human cancer patients (e.g., by administering an amount of an antibody or antigen binding fragment that is effective to stimulate proliferation of CD8+ T cells).

In one aspect, this document features an isolated heavy chain variable region polypeptide that binds specifically to TNFRSF25, where the polypeptide includes heavy chain CDR1, CDR2, and CDR3 sequences, where the CDR1 sequence is GFTFSNHDLN (SEQ ID NO:4), the CDR2 sequence is YISSASGLISYADAVRG (SEQ ID NO:6); and (c) the CDR3 sequence is DPPYSGLYALDF (SEQ ID NO:8). The isolated heavy chain variable region polypeptide can further include variable region heavy chain framework (FW) sequences juxtaposed between the heavy chain CDRs according to the formula (FW1)-(CDR1)-(FW2)-(CDR2)-(FW3)-(CDR3)-(FW4). The heavy chain framework sequences can be human. In some embodiments, the isolated heavy chain variable region polypeptide can be combination with a light chain variable region polypeptide comprising light chain CDR1, CDR2, and CDR3 sequences, wherein the CDR1 sequence is TLSSELSSYTIV (SEQ ID NO:11), the CDR2 sequence is LKSDGSHSKGD (SEQ ID NO:13), and the CDR3 sequence is GAGYTLAGQYGWV (SEQ ID NO:15). Variable region light chain framework (FW) sequences can be juxtaposed between the light chain CDRs according to the formula (FW1)-(CDR1)-(FW2)-(CDR2)-(FW3)-(CDR3)-(FW4). The light chain framework sequences can be human.

In another aspect, this document features an isolated anti-TNFRSF25 antibody or antigen binding fragment thereof, where the antibody or antibody fragment contains (i) a heavy chain variable region sequence containing the amino acid sequence set forth in SEQ ID NO:1 or the amino acid sequence of SEQ ID NO:1 with no more than 12 total amino acid substitutions, and (ii) a light chain variable region sequence containing the amino acid sequence of SEQ ID NO:2 or the amino acid sequence of SEQ ID NO:2 with no more than 11 total amino acid substitutions. The antibody or antigen binding fragment can further include a human constant region (e.g., a constant region selected from the group consisting of human IgG1, IgG2, IgG3, and IgG4), or a murine constant region (e.g., a constant region selected from the group consisting of murine IgG1, IgG2A, IgG2B, and IgG3). The antibody or antigen binding fragment can have reduced or minimal effector function. The antibody or antigen binding fragment can bind to human TNFRSF25 with an affinity of about 5 nM. The antibody or antigen binding fragment can be capable of increasing proliferation of human, murine, or macaque T cells in vitro or in vivo (e.g., wherein the proliferation of the T cell is increased by at least 20%, as determined by flow cytometry analysis of antigen specific T cells). Administration of the antibody or antigen binding fragment to a subject at a dose of about of 0.1 mg/kg to about 50 mg/kg can lead to stimulation of T cell proliferation in the subject, and/or to increased tumor cell apoptosis in the subject.

This document also features a pharmaceutical composition containing a pharmaceutically acceptable carrier and an antibody or antigen binding fragment as described herein.

In addition, this document features an article of manufacture containing a pharmaceutical composition as provided herein and at least one additional agent for treating cancer. The at least one additional agent can include, for example, an agent that targets CTLA-4, PD-1, PD-L1, LAG-3, Tim-3, TNFRSF4, TNFRSF9, TNFRSF18, CD27, CD39, CD47, CD73, or CD278, an A2A receptor antagonist, a TGF-beta antagonist, a B7 family costimulatory molecule, a TNF receptor superfamily costimulatory molecule, a vaccine composition, chimeric antigen receptor-transfected T cells or expanded tumor infiltrating lymphocytes for use in an adoptive T cell therapy (e.g., in vitro or in a subject), or a chemotherapeutic agent. In some embodiments, the at least one additional agent can be used during the in vitro manufacturing process of an autologous T cell therapy.

In another aspect, this document features an isolated monoclonal antibody that specifically binds to TNFRSF25. The antibody can include (a) a heavy chain containing a CDR1 sequence as set forth in SEQ ID NO:4, a CDR2 sequence as set forth in SEQ ID NO:6, and a CDR3 sequence as set forth in SEQ ID NO:8, and (b) a light chain containing a CDR1 sequence as set forth in SEQ ID NO:11, a CDR2 sequence as set forth in SEQ ID NO:13, and a CDR3 sequence as set forth in SEQ ID NO:15. The isolated monoclonal antibody can include a heavy chain containing SEQ ID NO:1, 17, 21, 23, or 25, and a light chain comprising SEQ ID NO:2, 26, or 30.

In another aspect, this document features a pharmaceutical composition containing a pharmaceutically acceptable carrier and a human or humanized monoclonal antibody that specifically binds to TNFRSF25, where the antibody comprises includes (a) a heavy chain containing a CDR1 sequence as set forth in SEQ ID NO:4, a CDR2 sequence as set forth in SEQ ID NO:6, and a CDR3 sequence as set forth in SEQ ID NO:8, and (b) a light chain containing a CDR1 sequence as set forth in SEQ ID NO:11, a CDR2 sequence as set forth in SEQ ID NO:13, and a CDR3 sequence as set forth in SEQ ID NO:15. In some embodiments, the antibody can include a heavy chain comprising the amino acid sequence set forth in SEQ ID NO:1, 17, 21, 23, or 25, and a light chain comprising the amino acid sequence set forth in SEQ ID NO:2, 26, or 30.

In still another aspect, this document features an isolated monoclonal antibody that binds specifically to TNFRSF25, where the antibody contains a set of six CDRs that includes no more than four total amino acid substitutions in the set of six CDRs having the amino acid sequences set forth in SEQ ID NOS:4, 6, 8, 11, 13, and 15. In some embodiments, the set of six CDRs includes no more than two total amino acid substitutions in the set of six CDRs having the amino acid sequences set forth in SEQ ID NOS:4, 6, 8, 11, 13, and 15.

In another aspect, this document features a pharmaceutical composition containing a pharmaceutically acceptable carrier and a human or humanized monoclonal antibody that binds specifically to TNFRSF25, where the antibody contains a set of six CDRs that includes no more than four total amino acid substitutions in the set of six CDRs having the amino acid sequences set forth in SEQ ID NOS:4, 6, 8, 11, 13, and 15. In some embodiments, the set of six CDRs includes no more than two total amino acid substitutions in the set of six CDRs having the amino acid sequences set forth in SEQ ID NOS:4, 6, 8, 11, 13, and 15.

This document also features a method for treating a tumor in a subject. The method can include administering to the subject an amount of a composition as provided herein that is effective to induce apoptosis of TNFRSF25-expressing tumor cells in the tumor. The composition can include, for example, a pharmaceutically acceptable carrier and a human or humanized monoclonal antibody that binds specifically to TNFRSF25, where the antibody includes a set of six CDRs that comprises no more than four total amino acid substitutions in the set of six CDRs having the amino acid sequences set forth in SEQ ID NOS:4, 6, 8, 11, 13, and 15, or an isolated anti-TNFRSF25 antibody or antigen binding fragment thereof that includes (i) a heavy chain variable region sequence containing the amino acid sequence set forth in SEQ ID NO:1 or the amino acid sequence of SEQ ID NO:1 with no more than 12 total amino acid substitutions, and (ii) a light chain variable region sequence containing the amino acid sequence of SEQ ID NO:2 or the amino acid sequence of SEQ ID NO:2 with no more than 11 total amino acid substitutions.

In addition, this document features a method for stimulating proliferation of CD8+ T cells in a subject. The method can include administering to the subject a therapeutically effective amount of a composition as provided herein. Proliferation of CD8+ T cells can be increased by at least about 20% as compared to the baseline level of proliferation prior to the administering, as determined by flow cytometry analysis of antigen specific CD8+ T cells.

In yet another aspect, this document features a method for eliciting an immune response in a subject. The method can include administering to the subject a therapeutically effective amount of a composition as provided herein.

This document also features a method for stimulating proliferation of CD4+FoxP3+ regulatory T cells in a subject. The method can include administering to the subject a therapeutically effective amount of a composition as provided herein. Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4 is a scheme for TNFRSF25 antibody humanization.

DETAILED DESCRIPTION

Figure 1:
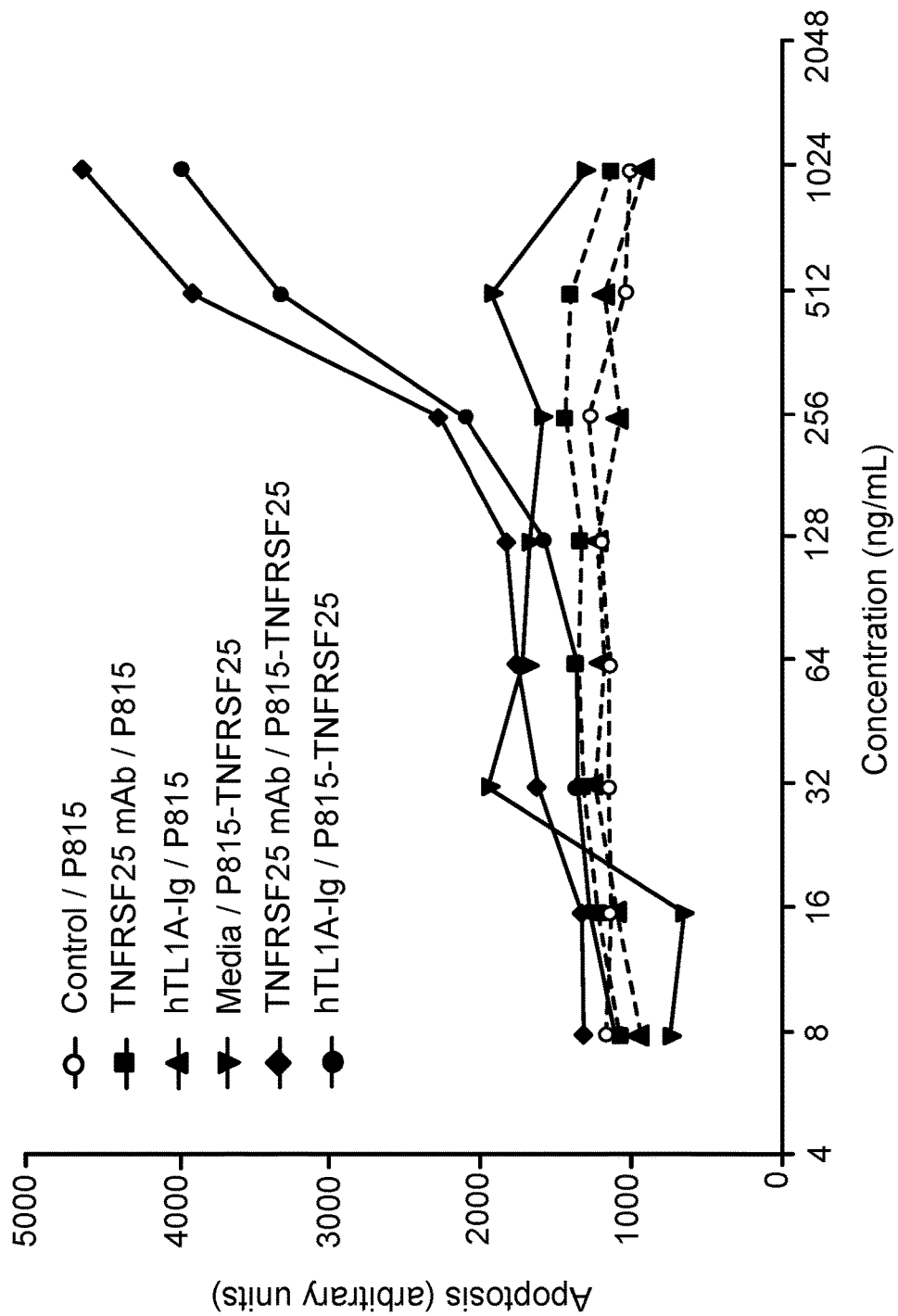
FIG. 1 is a graph plotting functional activity of a human TNFRSF25-specific mAb (PTX-25). P815 cells, or P815 cells expressing human TNFRSF25, were exposed in vitro to control human IgG, human TL1A-Ig, or PTX-25, as indicated. Functional activity of TNFRSF25 was determined by detection of caspase activation in cells expressing human TNFRSF25 and exposed to a TNFRSF25 agonist (human TL1A-Ig or PTX-25) as compared to control. Human TL1A-Ig and PTX-25 led to caspase activation in P815 cells expressing human TNFRSF25, but not in P815 cells alone.

This document provides a human TNFRSF25 specific monoclonal antibody ("PTX-25"), as well as humanized versions of the antibody, and antigen binding fragments of the antibody and its humanized versions. Also provided herein are methods for using PTX-25 to, inter alia, stimulate proliferation of T cells (e.g., human T cells, murine T cells, or macaque T cells), as well as methods for using PTX-25 in the treatment of human cancer patients (e.g., by administering an amount of PTX-25 that is effective to stimulate proliferation of CD8+ T cells).

As used herein, the term "antibody" refers to any immunoglobulin or antibody (e.g., human, hamster, feline, mouse, cartilaginous fish, or camelid antibodies), and any derivative or conjugate thereof, that specifically binds to an antigen. A wide variety of antibodies are known by those skilled in the art. Non-limiting examples of antibodies include monoclonal antibodies, polyclonal antibodies, humanized antibodies, multi-specific antibodies (e.g., bi-specific antibodies), single-chain antibodies (e.g., single-domain antibodies, camelid antibodies, and cartilaginous fish antibodies), chimeric antibodies, feline antibodies, and felinized antibodies. The term antibody also includes antibody derivatives and conjugates (e.g., an antibody conjugated to a stabilizing protein, a detectable moiety, or a therapeutic agent).

By "isolated" or "purified" with respect to a polypeptide (e.g., an antibody or a fragment thereof), it is meant that the polypeptide is separated to some extent from the cellular components with which would normally be found in nature (e.g., other polypeptides, lipids, carbohydrates, and nucleic acids). In some embodiments, an "isolated" polypeptide is one that is expressed and produced in an environment other than the environment in which the polypeptide would naturally expressed and produced. For example, a plant polypeptide is isolated when expressed and produced in bacteria or fungi. Similarly, a plant polypeptide is isolated when its gene coding sequence is operably linked to a chimeric regulatory element and expressed in a tissue where the polypeptide is not naturally expressed.

An isolated polypeptide can yield a single major band on a non-reducing polyacrylamide gel. An isolated polypeptide can be at least about 75% pure (e.g., at least 80%, 85%, 90%, 95%, 97%, 98%, 99%, or 100% pure). Isolated polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

An "antigen binding fragment" is any portion of a full-length antibody that contains at least one variable domain (e.g., a variable domain of a mammalian (e.g., feline, human, hamster, or mouse) heavy or light chain immunoglobulin, a camelid variable antigen binding domain (VHH), or a cartilaginous fish immunoglobulin new antigen receptor (Ig-NAR) domain) that is capable of specifically binding to an antigen. Non-limiting examples of antibody fragments include Fab, Fab', F(ab')$_2$, and Fv fragments, diabodies, linear antibodies, and multi-specific antibodies formed from antibody fragments. Additional antibody fragments containing at least one camelid VHH domain or at least one cartilaginous fish Ig-NAR domain include mini-bodies, micro-antibodies, subnano-antibodies, and nano-antibodies, and any of the other forms of antibodies described, for example, in U.S. Publication No. 2010/0092470.

An "Fv fragment" is the minimum antibody fragment that contains a complete antigen recognition and binding site. This region consists of a dimer of one heavy chain variable domain and one light chain variable domain in tight, non-covalent association. It is in this configuration that the three complementary determining regions (CDRs) of each variable domain interact to define an antigen binding site on the surface of the VH-VL dimer. As used herein, the term "complementary determining region" or "CDR" refers to a region within an immunoglobulin (a heavy or light chain immunoglobulin) that forms part of an antigen binding site in an antibody or antigen binding fragment thereof. As is known in the art, heavy chain and light chain immunoglobulins each contain three CDRs, referred to as CDR1, CDR2, and CDR3. In any antibody or antigen binding fragment, the three CDRs from the heavy chain immunoglobulin and the three CDRs from the light chain immunoglobulin together form an antigen binding site in the antibody or antigen binding fragment thereof. The Kabat Database is one system used in the art to number CDR sequences present in a light chain immunoglobulin or a heavy chain immunoglobulin.

Collectively, the six CDR's confer antigen binding specificity to the antibody. However, even a single variable domain (or half of an Fv comprising only three CDR's specific for an antigen) has the ability to recognize and bind the antigen, although usually at a lower affinity than the entire binding site. The "Fab fragment" also contains the constant domain of the light chain and the first constant domain ($C_H1$) of the heavy chain. The "Fab fragment" differs from the "Fab' fragment" by the addition of a few residues at the carboxy terminus of the heavy chain $C_H1$ domain, including one or more cysteines from the antibody hinge region. The "F(ab')2 fragment" originally is produced as a pair of "Fab' fragments" which have hinge cysteines between them. Methods of preparing such antibody fragments, such as papain or pepsin digestion, are known to those skilled in the art.

An antibody can be of the IgA-, IgD-, IgE, IgG- or IgM-type, including IgG- or IgM-types such as, without limitation, IgG1-, IgG2-, IgG3-, IgG4-, IgM1- and IgM2-types. For example, in some cases, the antibody is of the IgG1-, IgG2- or IgG4-type.

In some embodiments, antibodies as provided herein can be fully human or humanized antibodies. By "human antibody" is meant an antibody that is encoded by a nucleic acid (e.g., a rearranged human immunoglobulin heavy or light chain locus) present in the genome of a human. In some embodiments, a human antibody can be produced in a human cell culture (e.g., feline hybridoma cells). In some embodiments, a human antibody can be produced in a non-human cell (e.g., a mouse or hamster cell line). In some embodiments, a human antibody can be produced in a bacterial or yeast cell.

Human antibodies can avoid certain problems associated with xenogeneic antibodies, such as antibodies that possess murine or rat variable and/or constant regions. For example, because the effector portion is human, it can interact better with other parts of the human immune system, e.g., to destroy target cells more efficiently by complement-dependent cytotoxicity or antibody-dependent cellular cytotoxicity. In addition, the human immune system should not recognize the antibody as foreign. Further, half-life in human circulation will be similar to naturally occurring human antibodies, allowing smaller and less frequent doses to be given. Methods for preparing human antibodies are known in the art.

As used herein, the term "humanized antibody" refers to a human antibody that contains minimal sequence derived from non-human (e.g., mouse, hamster, rat, rabbit, or goat) immunoglobulin. Humanized antibodies generally are chimeric or mutant monoclonal antibodies from mouse, rat, hamster, rabbit or other species, bearing human constant and/or variable region domains or specific changes. In non-limiting examples, humanized antibodies are human antibodies (recipient antibody) in which hypervariable region (HVR) residues of the recipient antibody are replaced by HVR residues from a non-human species (donor) antibody, such as a mouse, rat, rabbit, or goat antibody having the desired specificity, affinity, and capacity. In some embodiments, Fv framework residues of the human immunoglobulin can be replaced by corresponding non-human residues. In some embodiments, humanized antibodies can contain residues that are not found in the recipient antibody or in the donor antibody. Such modifications can be made to refine antibody performance, for example.

In some embodiments, a humanized antibody can contain substantially all of at least one, and typically two, variable domains, in which all or substantially all of the hypervariable loops (CDRs) correspond to those of a non-human immunoglobulin, while all or substantially all of the framework regions are those of a human immunoglobulin sequence. A humanized antibody also can contain at least a portion of an immunoglobulin constant (Fc) region, typically that of a human immunoglobulin.

In some embodiments, humanized antibody or antigen binding fragment as provided herein can have reduced or minimal effector function (e.g., as compared to corresponding, non-humanized antibody), such that it does not stimulate effector cell action to the same extent that a corresponding non-humanized antibody would.

Techniques for generating humanized antibodies are well known to those of skill in the art. In some embodiments, controlled rearrangement of antibody domains joined through protein disulfide bonds to form new, artificial protein molecules or "chimeric" antibodies can be utilized (Konieczny et al., *Haematologia* (*Budap.*) 14:95, 1981). Recombinant DNA technology can be used to construct gene fusions between DNA sequences encoding mouse antibody variable light and heavy chain domains and human antibody light and heavy chain constant domains (Morrison et al., *Proc Natl Acad Sci USA* 81:6851, 1984). For example, DNA sequences encoding antigen binding portions or CDRs of murine monoclonal antibodies can be grafted by molecular means into DNA sequences encoding frameworks of human antibody heavy and light chains (Jones et al., *Nature* 321:522, 1986; and Riechmann et al., *Nature* 332:323, 1988). Expressed recombinant products are called "reshaped" or humanized antibodies, and contain the framework of a human antibody light or heavy chain and antigen recognition portions, CDRs, of a murine monoclonal antibody.

Other methods for designing heavy and light chains and for producing humanized antibodies are described in, for example, U.S. Pat. Nos. 5,530,101; 5,565,332; 5,585,089; 5,639,641; 5,693,761; 5,693,762; and 5,733,743. Yet additional methods for humanizing antibodies are described in U.S. Pat. Nos. 4,816,567; 4,935,496; 5,502,167; 5,558,864; 5,693,493; 5,698,417; 5,705,154; 5,750,078; and 5,770,403, for example.

The term "single-chain antibody" refers to a single polypeptide that contains at least one variable binding domain (e.g., a variable domain of a mammalian heavy or light chain immunoglobulin, a camelid VHH, or a cartilaginous fish (e.g., shark) Ig-NAR domain) that is capable of specifically binding to an antigen. Non-limiting examples of single-chain antibodies include single-domain antibodies.

As used herein, the term "single-domain antibody" refers to a polypeptide that contains one camelid VHH or at least one cartilaginous fish Ig-NAR domain that is capable of specifically binding to an antigen. Non-limiting examples of single-domain antibodies are described, for example, in U.S. Publication No. 2010/0092470.

Figure 6:
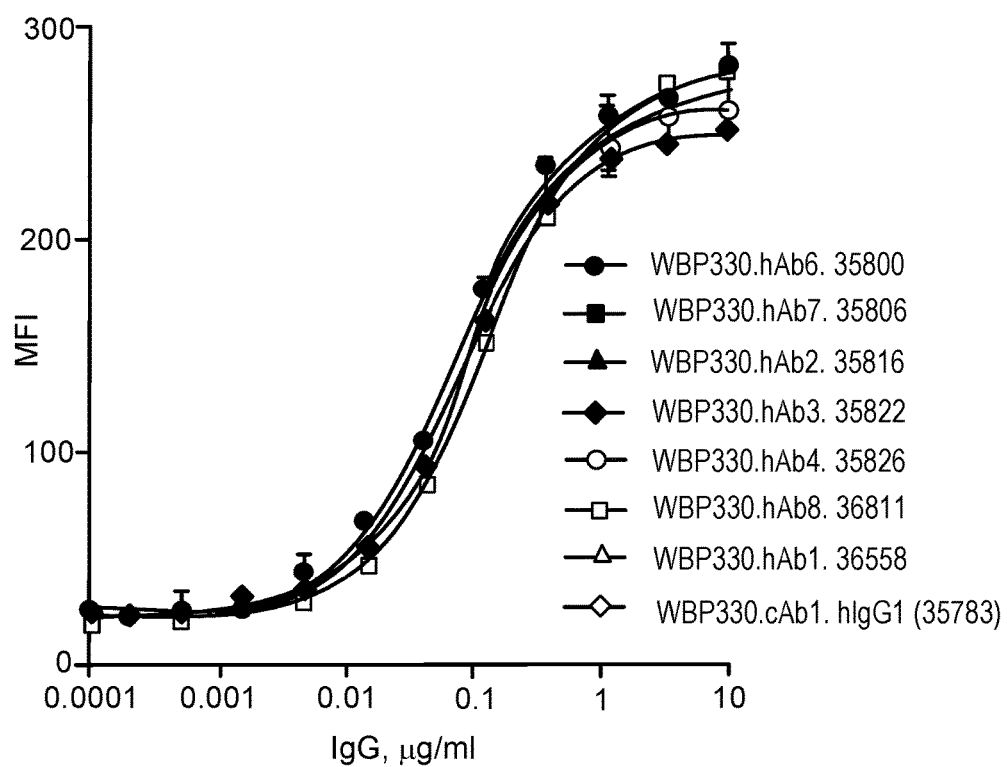
FIG. 6 is a graph plotting flow cytometry binding of humanized clones to P815 cells expressing human TNFRSF25.
Figure 7:
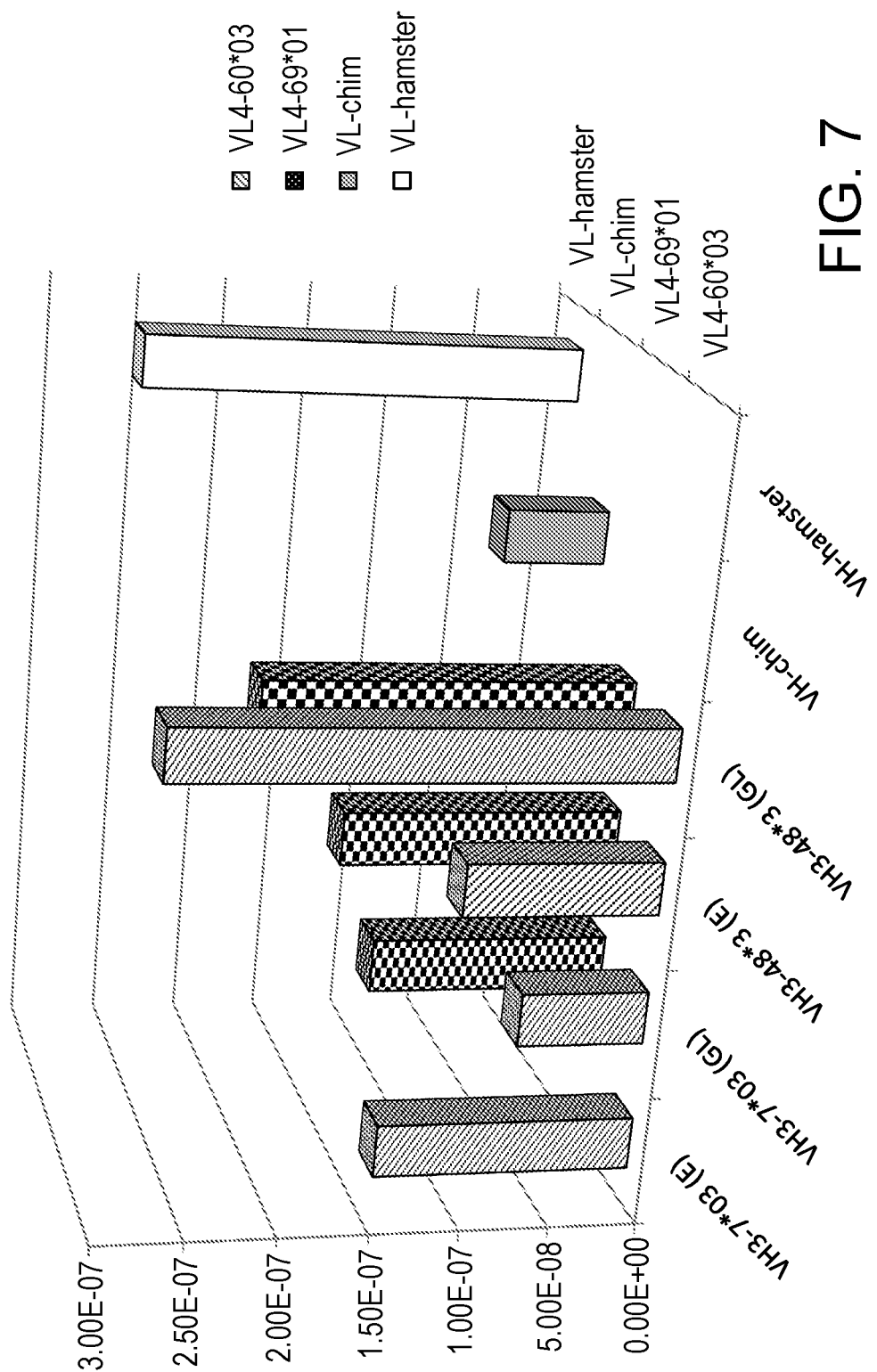
FIG. 7 is a graph plotting surface plasmon resonance affinity for humanized antibody clones.

An antibody or antigen binding fragment thereof "specifically binds" to a particular antigen, e.g., TNFRFS25, when it binds to that antigen in a sample, and does not recognize and bind, or recognizes and binds to a lesser extent, other molecules in the sample. In some embodiments, an antibody or an antigen binding fragment thereof can selectively bind to an epitope with an affinity ($K_D$) equal to or less than, for example, about $1 \times 10^{-6}$ M (e.g., equal to or less than about $1 \times 10^{-9}$ M, equal to or less than about $1 \times 10^{-10}$ M, equal to or less than about $1 \times 10^{-11}$ M, or equal to or less than about $1 \times 10^{-12}$ M) in phosphate buffered saline. The ability of an antibody or antigen binding fragment to specifically bind a protein epitope can be determined using any of the methods known in the art or those methods described herein. This can include, for example, binding to TNFRSF25 on live cells as a method to stimulate caspase activation in live transformed cells (FIG. 2 and TABLE 1), binding to an immobilized target substrate including human TNFRSF25 fusion proteins as detected using an ELISA method (FIG. 3), binding to TNFRSF25 on live cells as detected by flow cytometry (FIG. 6 and TABLE 2), or binding to an immobilized substrate by surface plasmon resonance (including ProteOn) (FIG. 7 and TABLE 3).

As described herein, a monoclonal antibody against TNFRSF25 was isolated, and the amino acid sequences of the variable heavy and light chains were determined to contain SEQ ID NOS:1 and 2, respectively. As described in Example 4 below, the antibody was humanized, such that several humanized VH (SEQ ID NOS:17, 21, 23, and 25) and VL (SEQ ID NOS:26 and 30) genes were designed using homologous frameworks of human germ line genes (FIG. 4).

Thus, this document provides heavy chain variable region polypeptides containing the amino acid sequence set forth in SEQ ID NO:1, 17, 21, 23, or 25, or an antigen binding fragment thereof, as well as polypeptides having at least about 90% (e.g., about 91%, about 92%, about 93%, about 94%, about 95%, about 96%, about 97%, about 98%, or about 99%) amino acid sequence identity to SEQ ID NO:1, 17, 21, 23, or 25, or an antigen binding fragment thereof. In some embodiments, a heavy chain variable region polypeptide can contain 12 or less (e.g., 12, 11, ten, nine, eight, seven, six, five, four, three, two, or one) amino acid substitution as compared to SEQ ID NO:1, 17, 21, 23, or 25, or an antigen binding fragment thereof.

In some embodiments, a heavy chain variable region polypeptide can include the CDR1 sequence set forth in SEQ ID NO:4, the CDR2 sequence set forth in SEQ ID NO:6, and the CDR3 sequence set forth in SEQ ID NO:8. The polypeptide also can include variable region heavy chain framework (FW) sequences juxtaposed between the CDRs, according to the formula (FW1)-(CDR1)-(FW2)-(CDR2)-(FW3)-(CDR3)-(FW4), for example. In some embodiments, the FW sequences can be human sequences. In some embodiments, a heavy chain variable region polypeptide can include the FW1 sequence set forth in SEQ ID NO:3, SEQ ID NO:18, or SEQ ID NO:22, the FW2 sequence set forth in SEQ ID NO:5, SEQ ID NO:19, or SEQ ID NO:24, the FW3 sequence set forth in SEQ ID NO:7 or SEQ ID NO:20, and the FW4 sequence set forth in SEQ ID NO:9. Particular combinations of heavy chain variable region CDR and FW sequences are set forth in the Examples herein. It is to be noted, however, that this document contemplates other combinations of the disclosed CDR and FW sequences.

This document also provides light chain variable region polypeptides containing the amino acid sequence set forth in SEQ ID NO:2, 26, or 30, or an antigen binding fragment thereof, as well as polypeptides having at least about 90% (e.g., about 91%, about 92%, about 93%, about 94%, about 95%, about 96%, about 97%, about 98%, or about 99%) amino acid sequence identity to SEQ ID NO:2, 26, or 30, or an antigen binding fragment thereof. In some embodiments, a light chain variable region polypeptide can contain 11 or less (e.g., 11, ten, nine, eight, seven, six, five, four, three, two, or one) amino acid substitutions as compared to SEQ ID NO:2, 26, or 30, or an antigen binding fragment thereof.

In some embodiments, a light chain variable region polypeptide can contain the CDR1 sequence set forth in SEQ ID NO:11, the CDR2 sequence set forth in SEQ ID NO:13, and the CDR3 sequence set forth in SEQ ID NO:15. The polypeptide also can include variable region light chain FW juxtaposed between the CDRs, according to the formula (FW1)-(CDR1)-(FW2)-(CDR2)-(FW3)-(CDR3)-(FW4). In some cases, the FW sequences can be human sequences. In some embodiments, a light chain variable region polypeptide can include the FW1 sequence set forth in SEQ ID NO:10, SEQ ID NO:27, or SEQ ID NO:31, the FW2 sequence set forth in SEQ ID NO:12, SEQ ID NO:28, or SEQ ID NO:32, the FW3 sequence set forth in SEQ ID NO:14, SEQ ID NO:29, or SEQ ID NO:33, and the FW4 sequence set forth in SEQ ID NO:16. Particular combinations of light chain variable region CDR and FW sequences are set forth in the Examples herein. It is to be noted, however, that this document contemplates other combinations of the disclosed CDR and FW sequences.

This document also provides antibodies and antigen binding fragments that contain both a heavy chain variable region polypeptide and a light chain variable region polypeptide as disclosed herein. In some embodiments, for example, an antibody or antigen binding fragment can contain both a heavy chain variable region sequence comprising the amino acid sequence set forth in SEQ ID NO:1, or the amino acid sequence of SEQ ID NO:1 with no more than 12 total amino acid substitutions (e.g., no more than ten, no more than eight, no more than six, no more than four, or no more than two total amino acid substitutions), and a light chain variable region sequence comprising the amino acid sequence of SEQ ID NO:2, or the amino acid sequence of SEQ ID NO:2 with no more than 11 total amino acid substitutions (e.g., no more than nine, no more than seven, no more than five, no more than three, or no more than one total amino acid substitution). An amino acid substitution refers to the replacement of one amino acid residue with another in a peptide sequence.

In some embodiments, amino acid substitutions can be made by selecting conservative substitutions that do not differ significantly in their effect on maintaining (a) the structure of the peptide backbone in the area of the substitution, (b) the charge or hydrophobicity of the molecule at the target site, or (c) the bulk of the side chain. For example, naturally occurring residues can be divided into groups based on side-chain properties: (1) hydrophobic amino acids (norleucine, methionine, alanine, valine, leucine, and isoleucine); (2) neutral hydrophilic amino acids (cysteine, serine, and threonine); (3) acidic amino acids (aspartic acid and glutamic acid); (4) basic amino acids (asparagine, glutamine, histidine, lysine, and arginine); (5) amino acids that influence chain orientation (glycine and proline); and (6) aromatic amino acids (tryptophan, tyrosine, and phenylalanine). Substitutions made within these groups can be considered conservative substitutions. Non-limiting examples of conservative substitutions include, without limitation, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine. In some embodiments, an amino acid substitution can be non-conservative, such that a member of one of the amino acid classes described above is exchanged for a member of another class.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -1 -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:1), or by an articulated length (e.g., 100 consecutive nucleotides or amino acid residues from a sequence set forth in an identified sequence), followed by multiplying the resulting value by 100. For example, an amino acid sequence that has 110 matches when aligned with the sequence set forth in SEQ ID NO:1 is 90.9 percent identical to the sequence set forth in SEQ ID NO:1 (i.e., 110÷121×100=90.9). It is noted that the percent sequence identity value is rounded to the nearest tenth. For example, 75.11, 75.12, 75.13, and 75.14 is rounded down to 75.1, while 75.15, 75.16, 75.17, 75.18, and 75.19 is rounded up to 75.2. It also is noted that the length value will always be an integer.

This document also provides pharmaceutical compositions that contain an antibody or antigen binding fragment as described herein, in combination with a pharmaceutically acceptable carrier. A "pharmaceutically acceptable carrier" (also referred to as an "excipient" or a "carrier") is a pharmaceutically acceptable solvent, suspending agent, stabilizing agent, or any other pharmacologically inert vehicle for delivering one or more therapeutic compounds to a subject (e.g., a mammal, such as a human, non-human primate, dog, cat, sheep, pig, horse, cow, mouse, rat, or rabbit), which is nontoxic to the cell or subject being exposed thereto at the dosages and concentrations employed. Pharmaceutically acceptable carriers can be liquid or solid, and can be selected with the planned manner of administration in mind so as to provide for the desired bulk, consistency, and other pertinent transport and chemical properties, when combined with one or more of therapeutic compounds and any other components of a given pharmaceutical composition. Typical pharmaceutically acceptable carriers that do not deleteriously react with amino acids include, by way of example and not limitation: water, saline solution, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). Pharmaceutically acceptable carriers also include aqueous pH buffered solutions or liposomes (small vesicles composed of various types of lipids, phospholipids and/or surfactants which are useful for delivery of a drug to a mammal). Further examples of pharmaceutically acceptable carriers include buffers such as phosphate, citrate, and other organic acids, antioxidants such as ascorbic acid, low molecular weight (less than about 10 residues) polypeptides, proteins such as serum albumin, gelatin, or immunoglobulins, hydrophilic polymers such as polyvinylpyrrolidone, amino acids such as glycine, glutamine, asparagine, arginine or lysine, monosaccharides, disaccharides, and other carbohydrates including glucose, mannose or dextrins, chelating agents such as EDTA, sugar alcohols such as mannitol or sorbitol, salt-forming counterions such as sodium, and/or nonionic surfactants such as TWEEN™, polyethylene glycol (PEG), and PLURONICS™.

Pharmaceutical compositions can be formulated by mixing one or more active agents with one or more physiologically acceptable carriers, diluents, and/or adjuvants, and optionally other agents that are usually incorporated into formulations to provide improved transfer, delivery, tolerance, and the like. A pharmaceutical composition can be formulated, e.g., in lyophilized formulations, aqueous solutions, dispersions, or solid preparations, such as tablets, dragees or capsules. A multitude of appropriate formulations can be found in the formulary known to all pharmaceutical chemists: *Remington's Pharmaceutical Sciences* (18th ed, Mack Publishing Company, Easton, Pa. (1990)), particularly Chapter 87 by Block, Lawrence, therein. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies as described herein, provided that the active agent in the formulation is not inactivated by the formulation and the formulation is physiologically compatible and tolerable with the route of administration. See, also, Baldrick, *Regul Toxicol Pharmacol* 32:210-218, 2000; Wang, *Int J Pharm* 203:1-60, 2000; Charman *J Pharm Sci* 89:967-978, 2000; and Powell et al. *PDA J Pharm Sci Technol* 52:238-311, 1998), and the citations therein for additional information related to formulations, excipients and carriers well known to pharmaceutical chemists.

Pharmaceutical compositions include, without limitation, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations have been widely used for oral delivery of therapeutics due to their ease of formulation and efficacy of solubilization, absorption, and bioavailability.

Compositions and formulations can contain sterile aqueous solutions, which also can contain buffers, diluents and other suitable additives (e.g., penetration enhancers, carrier compounds and other pharmaceutically acceptable carriers). Compositions additionally can contain other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the polypeptide components within the compositions provided herein. The formulations can be sterilized if desired.

In some embodiments, a composition containing an antibody or antigen binding fragment as provided herein (e.g., PTX-25 or an antigen binding fragment thereof) can be in the form of a solution or powder with or without a diluent to make an injectable suspension. The composition may contain additional ingredients including, without limitation, pharmaceutically acceptable vehicles, such as saline, water, lactic acid, mannitol, or combinations thereof, for example.

Any appropriate method can be used to administer an antibody or antigen binding fragment as described herein to a mammal. Administration can be, for example, parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations). In some embodiments, administration can be topical (e.g., transdermal, sublingual, ophthalmic, or intranasal), pulmonary (e.g., by inhalation or insufflation of powders or aerosols), or oral. In addition, a composition containing an antibody or antigen binding fragment as described herein can be administered prior to, after, or in lieu of surgical resection of a tumor.

A composition containing an anti-TNFRSF25 antibody or antigen binding fragment can be administered to a mammal in any appropriate amount, at any appropriate frequency, and for any appropriate duration effective to achieve a desired outcome. For example, an anti-TNFRSF25 antibody or antigen binding fragment can be administered to a subject in an amount effective to stimulate proliferation of T cells in vitro or in vivo (e.g., human, murine, hamster, or macaque T cells, including CD8+ T cells and/or CD4+FoxP3+ regulatory T cells), to stimulate apoptosis of tumor cells that express TNFRSF25, to reduce tumor size, or to increase progression-free survival of a cancer patient.

Administration to a subject of an antibody or antigen binding fragment as provided herein can result in increased numbers of T cells (e.g., naturally-occurring tumor-reactive CD8+ T cells or CD4+FoxP3+ regulatory T cells) that can exert anti-cancer effects against cancer cells present within the mammal. Thus, this document also provides methods for stimulating proliferation of T cells in a subject, by administering to the subject an antibody, antigen-binding fragment, or composition as disclosed herein. In some cases, a composition containing an anti-TNFRSF25 antibody or antigen binding fragment as described herein can be administered to a subject in an amount effective to increase proliferation of T cells (e.g., by at least about 10 percent, about 20 percent, about 25 percent, about 50 percent, about 60 percent, about 70 percent, about 75 percent, about 80 percent, about 90 percent, about 100 percent, or more than 100 percent), as compared to the "baseline" level of T cell proliferation in the subject prior to administration of the composition, or as compared to the level of T cell proliferation in a control subject or population of subjects to whom the composition was not administered. The T cells can be, for example, CD8+ T cells, or CD4+FoxP3+ regulatory T cells. Any suitable method can be used to determine whether or not the level of T cell proliferation is increased in the subject. Such methods can include, without limitation, flow cytometry analysis of antigen specific T cells (e.g., flow cytometry analysis of the proportion of antigen specific CD8+ T cells as a fraction of the total CD8+ T cell pool), analysis of cell proliferation markers (e.g., expression of Ki67) in CD8+ T cells, increased counts of CD8+ T cells, or increased proportions of individual TCR sequences of a particular clone of CD8+ T cells.

This document also provides methods for promoting apoptosis of TNFRSF25-expressing tumor cells in a subject, by treating the subject with an antibody, antigen-binding fragment, or composition as described herein. In some cases, a composition containing an antibody or antigen binding fragment as provided herein can be administered to a subject (e.g., a cancer patient) in an amount effective to increase apoptosis of TNFRSF25-expressing tumor cells (e.g., by at least about 10 percent, about 20 percent, about 25 percent, about 50 percent, about 60 percent, about 70 percent, about 75 percent, about 80 percent, about 90 percent, about 100 percent, or more than 100 percent), as compared to the "baseline" level of tumor cell apoptosis in the subject prior to administration of the composition, or as compared to the level of tumor cell apoptosis in a control subject or population of subjects to whom the composition was not administered. Any suitable method can be used to determine whether or not the level of tumor cell apoptosis is increased in the subject. This can include, for example, radiologic techniques such as CT or MRI, with or without contrast that indicates the presence of a necrotic or apoptotic tumor, biopsy of a tumor sample indicating increased tumor cell death, caspase induction within tumor cells, elimination of detectable tumor lesions by radiologic, or surgical or physical examination.

Methods for treating a subject (e.g., a human patient) with cancer also are provided herein. In some cases, a composition containing an antibody or antigen binding fragment as described herein can be administered to a subject having cancer in an amount effective to reduce the progression rate of the cancer (e.g., by at least about 10 percent, about 20 percent, about 25 percent, about 50 percent, about 60 percent, about 70 percent, about 75 percent, about 80 percent, about 90 percent, or more than 90 percent), as compared to the rate of cancer progression in the subject prior to administration of the composition, or as compared to the rate of cancer progression in a control subject or population of subjects to whom the composition was not administered. In some embodiments, the progression rate can be reduced such that no additional cancer progression is detected. Any appropriate method can be used to determine whether or not the progression rate of cancer is reduced. For skin cancer (e.g., melanoma), for example, the progression rate can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer after treatment can be determined and compared to the stage before treatment to determine whether or not the progression rate has been reduced.

A composition containing an antibody or antigen binding fragment as described herein also can be administered to a subject having cancer under conditions where progression-free survival is increased (e.g., by at least about 10 percent, about 20 percent, about 25 percent, about 50 percent, about 60 percent, about 70 percent, about 75 percent, about 80 percent, about 90 percent, about 100 percent, or more than 100 percent), as compared to the median progression-free survival of corresponding subjects having untreated cancer or the median progression-free survival of corresponding subjects having cancer and treated with other therapies (e.g., chemotherapeutic agents alone).

Progression-free survival can be measured over any length of time (e.g., one month, two months, three months, four months, five months, six months, or longer).

An effective amount of a composition containing a molecule as provided herein can be any amount that has a desired defect (e.g., stimulates proliferation of CD8+ T cells, stimulates apoptosis of TNFRSF25-expressing tumor cells, stimulates or elicits an immune response in a subject, reduces tumor size, reduces the progression rate of cancer, increases progression-free survival of a cancer patient, or increases the median time to progression without producing significant toxicity). Optimum dosages can vary depending on the relative potency of individual polypeptides (e.g., antibodies and antigen binding fragments), and can generally be estimated based on $EC_{50}$ found to be effective in in vitro and in vivo animal models. Typically, dosage is from 0.01 µg to 100 g per kg of body weight. For example, an effective amount of an antibody or antigen binding fragment can be from about 0.1 mg/kg to about 50 mg/kg (e.g., about 0.4 mg/kg, about 2 mg/kg, about 5 mg/kg, about 10 mg/kg, about 20 mg/kg, about 30 mg/kg, about 40 mg/kg, or about 50 mg/kg), or any range there between, such as about 0.1 mg/kg to about 10 mg/kg, about 0.4 mg/kg to about 20 mg/kg, about 2 mg/kg to about 30 mg/kg, or about 5 mg/kg to about 40 mg/kg. If a particular subject fails to respond to a particular amount, then the amount of the antibody or antigen binding fragment can be increased by, for example, two fold. After receiving this higher concentration, the subject can be monitored for both responsiveness to the treatment and toxicity symptoms, and adjustments made accordingly. The effective amount can remain constant or can be adjusted as a sliding scale or variable dose depending on the subject's response to treatment. Various factors can influence the actual effective amount used for a particular application. For example, the frequency of administration, duration of treatment, use of multiple treatment agents, route of administration, and severity of the cancer may require an increase or decrease in the actual effective amount administered.

The frequency of administration can be any frequency that, for example, stimulates proliferation of CD8+ T cells, stimulates apoptosis of TNFRSF25-expressing tumor cells, reduces tumor size, reduces the progression rate of cancer, increases progression-free survival of a cancer patient, or increases the median time to progression without producing significant toxicity. For example, the frequency of administration can be once or more daily, biweekly, weekly, monthly, or even less. The frequency of administration can remain constant or can be variable during the duration of treatment. A course of treatment can include rest periods. For example, a composition containing an antibody or antigen binding fragment as provided herein can be administered over a two week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition provided herein can be any duration that stimulates proliferation of CD8+ T cells, stimulates apoptosis of TNFRSF25-expressing tumor cells, reduces tumor size, reduces the progression rate of cancer, increases progression-free survival of a cancer patient, or increases the median time to progression without producing significant toxicity. Thus, an effective duration can vary from several days to several weeks, months, or years. In general, the effective duration for the treatment of cancer can range in duration from several weeks to several months. In some cases, an effective duration can be for as long as an individual subject is alive. Multiple factors can influence the actual effective duration used for a particular treatment. For example, an effective duration can vary with the frequency of administration, effective amount, use of multiple treatment agents, route of administration, and severity of the cancer.

After administering a composition as provided herein to a cancer patient, the patient can be monitored to determine whether or not the cancer was treated. For example, a subject can be assessed after treatment to determine whether or not the progression rate of the cancer has been reduced (e.g., stopped). Any method, including those that are standard in the art, can be used to assess progression and survival rates.

A method for using an antibody or antigen binding fragment as provided herein can be combined with known methods of treatment for cancer, for example, either as combined or additional treatment steps, or as additional components of a therapeutic formulation. For example, enhancing a host's immune function can be useful to combat tumors. Methods can include, without limitation, APC enhancement, such as by injection into a tumor of DNA encoding foreign MHC antigens (including tumor antigens, mutation derived antigens, or other antigens), or transfecting biopsied tumor cells with genes that increase the probability of immune antigen recognition (e.g., immune stimulatory cytokines, GM-CSF, or co-stimulatory molecules B7.1, B7.2) of the tumor. Other methods can include, for example, solubilization of specific tumor antigens into depot or sustained release preparations, transfection of allogeneic tumor cells with adjuvant proteins or antigen carrier proteins, transfection of allogeneic tumor cells with immune stimulatory proteins such as alpha galactosylceramide, incorporation of specific tumor antigens into virus-derived vaccine regimens, incorporation of specific tumor antigens into Listeria derived vaccine regimens, adoptive cellular immunotherapy (including chimeric antigen receptor transfected T cells), or treatment with activated tumor-specific T-cells (including ex vivo expanded tumor infiltrating lymphocytes). Adoptive cellular immunotherapy can include isolating tumor-infiltrating host T-lymphocytes and expanding the population in vitro (e.g., by stimulation with IL-2). The T-cells then can be re-administered to the host. Other treatments that can be used in combination with an antibody or antigen-binding fragment as provided herein include, for example, radiation therapy, chemotherapy, hormonal therapy, and the use of angiogenesis inhibitors.

Thus, in some embodiments, an anti-TNFRSF25 antibody or antigen binding fragment can be used in combination with one or more additional monoclonal antibodies that inhibit binding of PD-L1 to PD-1, inhibit binding of CTLA-4 to CD80 or CD86, or activate signaling via the TNFRSF4, TNFRSF9, or TNFRSF18 pathways, for example. This also can include administration with another antibody, fusion protein, or small molecule that binds a specific target on a tumor cell (e.g., combinations with monoclonal antibodies that bind targets such as CD20, Her2, EGFRvIII, DR4, DR5, VEGF, CD39, and CD73). An anti-TNFRSF25 antibody or antigen binding fragment also can be used in combination with a cancer vaccine approach to enhance the activation of tumor antigen specific T cells in a cancer patient. In addition, an anti-TNFRSF25 antibody or antigen binding fragment can be used after administration of autologous or allogeneic T or NK cells engineered to express a chimeric T cell receptor that recognizes a specific tumor antigen. Further, an anti-TNFRSF25 antibody or antigen binding fragment can be used in combination with specific chemotherapy or radiation therapy strategies as a method to expand tumor specific T cells and enhance the activity of either approach as a monotherapy in a cancer patient.

When one or more conventional therapies are combined with treatment using an anti-TNFRSF25 antibody or antigen binding fragment as provided herein for treating cancer, for example, the conventional therapy(ies) can be administered prior to, subsequent to, or simultaneously with administration of the anti-TNFRSF25 antibody or antigen binding fragment. For example, a PD-1 blocking antibody can be administered to a patient prior to administration of a TNFRSF25 agonist antibody. Such a regimen can be cycled over a period of weeks, months, or years, for example. Alternatively, a PD-1 blocking antibody can be administered at the same time or after administration of a TNFRSF25 agonist antibody. Such a regimen also can be cycled over a period of weeks, months, or years. In some embodiments, combination therapies that are repeatedly administered over a period of time can include two or more of the above administration strategies.

In some embodiments, an anti-TNFRSF25 antibody or antigen binding fragment as provided herein can be used during an in vitro assay or manufacturing process as a method for stimulating proliferation of tumor infiltrating lymphocytes isolated from a cancer patient, or to stimulate proliferation of chimeric antigen receptor expressing T cells being expanded in vitro and intended for subsequent infusion for the treatment of a cancer patient.

Also provided herein are articles of manufacture containing an antibody or antigen binding fragment as described herein, or a pharmaceutical composition containing the antibody or antigen binding fragment. The antibody or pharmaceutical composition can be within a container (e.g., a bottle, vial, or syringe). The article of manufacture also can include a label with directions for reconstituting and/or using the antibody, antigen binding fragment, or composition. In some embodiments, an article of manufacture can include one or more additional items (e.g., one or more buffers, diluents, filters, needles, syringes, and/or package inserts with further instructions for use). An article of manufacture also can include at least one additional agent for treating cancer. For example, an article of manufacture as provided herein can contain an agent that targets CTLA-4, PD-1, PD-L1, LAG-3, Tim-3, TNFRSF4, TNFRSF9, TNFRSF18, CD27, CD39, CD47, CD73, or CD278. In some embodiments, an article of manufacture can contain an A2A receptor antagonist or a TGF-beta antagonist. In some embodiments, an article of manufacture can include a B7 family costimulatory molecule (e.g., CD28 or CD278) or a TNF receptor superfamily costimulatory molecule (e.g., TNFRSF4, TNFRSF9, or TNFRSF18), a chemotherapeutic agent, or an anti-tumor vaccine composition.

The invention will be further described in the following examples, which do not limit the scope of the invention described in the claims.

EXAMPLES

Example 1

Functional Activity of Human PTX-25

Figure 2:
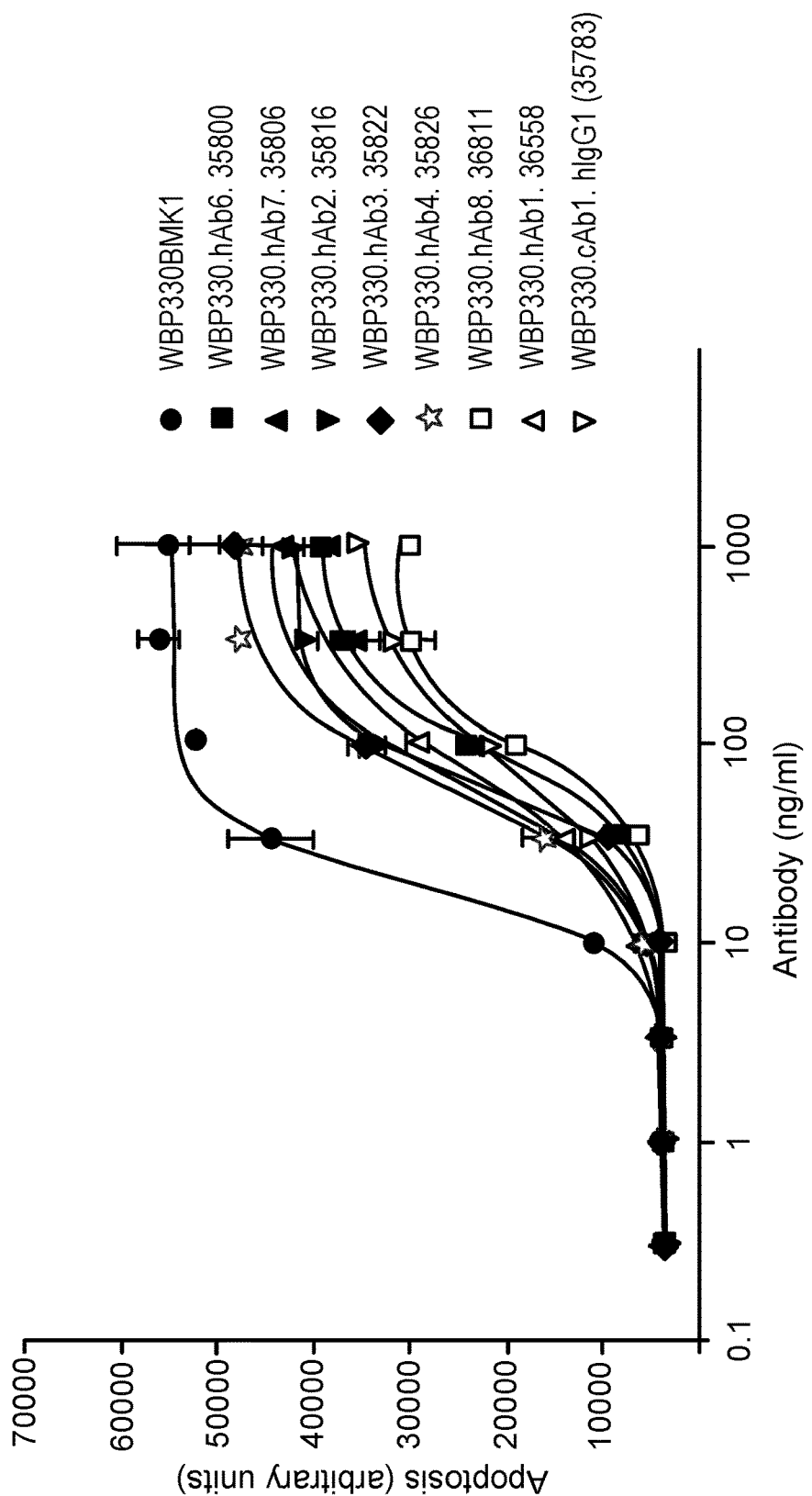
FIG. 2 is a graph plotting apoptosis of P815 cells expressing human TNFRSF25 and treated with the indicated humanized antibodies, as measured by caspase 3 activity.

P815 cells, or P815 cells expressing human TNFRSF25, were exposed in vitro to either control human IgG, human TL1A-Ig or PTX-25. TNFRSF25 contains a death domain, which can lead to apoptosis in cells with active signaling via TNFRSF25. Caspase activation can be used as a marker for cells that are undergoing apoptosis. Thus, functional activity of TNFRSF25 was determined by detection of caspase activation in cells expressing human TNFRSF25 and exposed to a TNFRSF25 agonist (human TL1A-Ig or PTX-25) as compared to control. Human TL1A-Ig and PTX-25, but not human IgG, led to caspase activation in P815 cells expressing human TNFRSF25, but not in P815 cells alone (FIG. 1). This assay also was performed using the various humanized constructs outlined herein. These data demonstrated an inverse relationship between the affinity of binding as determined by surface plasmon resonance and the functional activity as determined by caspase activation for the humanized constructs (FIG. 2 and TABLE 1).

Example 2

Binding of PTX-25 to Human TNFRSF25-Fc

Figure 3:
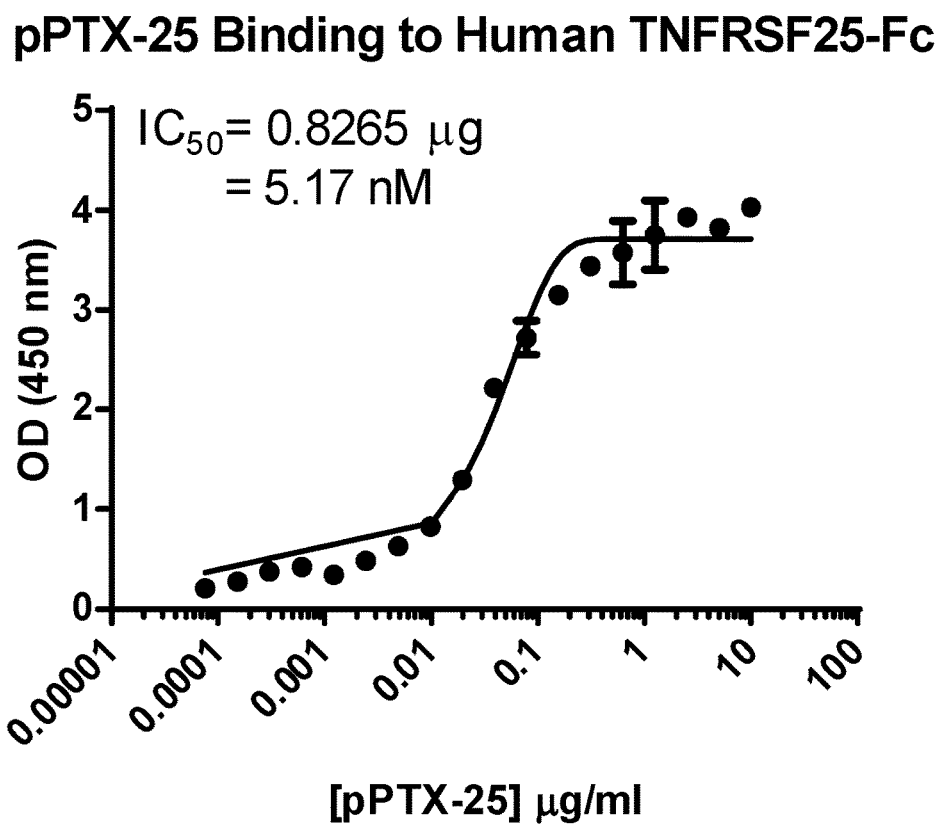
FIG. 3 is a graph plotting binding of PTX-25 to human TNFRSF25-Fc, as detected using an enzyme linked immunosorbent assay (ELISA).

The binding of PTX-25 to human TNFRSF25-Fc was detected and quantified using an enzyme linked immunosorbent assay (FIG. 3).

TABLE 1

|  | EC50 (nM) |
| --- | --- |
| WBP330BMK1 | 19.58 |
| WBP330.hAb6.35800 | 90.46 |
| WBP330.hAb7.35806 | 90.44 |
| WBP330.hAb2.35816 | 60.22 |
| WBP330.hAb3.35822 | 62.57 |
| WBP330.hAb4.35826 | 59.97 |
| WBP330.hAb8.36811 | 89.07 |
| WBP330.hAb1.36558 | 71.51 |
| WBP330.cAb1.hIgG1 (35783) | 71.38 |

Example 3

PTX-25 Amino Acid Sequences

Hybridoma sequencing yielded one hamster VH and one hamster VL (lambda) sequence. Protein sequences, including FW and CDR regions, are shown below. CDR definitions are Kabat with the exception of VH CDR1, which was defined using IMGT definition.

```
Pre-humanized Parental PTX-25 VH:
                                           (SEQ ID NO: 1)
EVQLVESGGGLSQPGNSLQLSCEASGFTFSNHDLNWVRQAPGKGLEWVAY

ISSASGLISYADAVRGRFTISRDNAKNSLFLQMNNLKSEDTAMYYCARDP

PYSGLYALDFWGQGTQVTVSS
```

FW1:
(SEQ ID NO: 3)
EVQLVESGGGLSQPGNSLQLSCEAS

CDR1:
(SEQ ID NO: 4)
GFTFSNHDLN

FW2:
(SEQ ID NO: 5)
WVRQAPGKGLEWVA

CDR2:
(SEQ ID NO: 6)
YISSASGLISYADAVRG

FW3:
(SEQ ID NO: 7)
RFTISRDNAKNSLFLQMNNLKSEDTAMYYCAR

CDR3:
(SEQ ID NO: 8)
DPPYSGLYALDF

FW4:
(SEQ ID NO: 9)
WGQGTQVTVSS

Pre-humanized Parental PTX-25 VL:
(SEQ ID NO: 2)
QPVLTQSPSASASLSGSVKLTCTLSSELSSYTIVWYQQRPDKAPKYVMYL
KSDGSHSKGDGIPDRFSGSSSGAHRYLSISNVQSEDDATYFCGAGYTLAG
QYGWVFGSGTKVTVL

FW1:
(SEQ ID NO: 10)
QPVLTQSPSASASLSGSVKLTC

CDR1:
(SEQ ID NO: 11)
TLSSELSSYTIV

FW2:
(SEQ ID NO: 12)
WYQQRPDKAPKYVMY

CDR2:
(SEQ ID NO: 13)
LKSDGSHSKGD

FW3:
(SEQ ID NO: 14)
GIPDRFSGSSSGAHRYLSISNVQSEDDATYFC

CDR3:
(SEQ ID NO: 15)
GAGYTLAGQYGWV

FW4:
(SEQ ID NO: 16)
FGSGTKVTVL

Example 4

Humanization of PTX-25

Four humanized VH-genes were designed using homologous frameworks of IGHV3-7*03 and IGHV3-48*03 human germ line genes. The amino acid after the Cys in the FW1 region was wobbled between human and mouse sequences (E and A), to better support CDR1 conformation. Two humanized VL-genes were designed using homologous frameworks of IGLV4-60*03 and IGLV4-69*01 human germ line genes. The scheme for humanization is illustrated in FIG. 4. The humanized V-genes were back-translated, codon optimized, and synthesized by GeneScript Custom Gene Synthesis. Seventeen antibodies, including one chimeric antibody and sixteen humanized antibodies (8 IgG1 and 8 IgG4), were expressed in 293F cells. Culture supernatants containing antibodies were harvested and purified using Protein A chromatography. Nucleic acid and encoded amino acid sequences follow.

Parental clone VH regions (79.6% human)
DNA:
(SEQ ID NO: 34)
GAGGTGCAGCTGGTGGAGTCTGGGGGAGGCTTATCACAGCCTGGAAATTC
CCTGCAACTCTCCTGTGAGGCCTCTGGATTCACCTTCAGTAATCATGATT
TGAACTGGGTCCGCCAGGCTCCAGGGAAGGGGCTGGAGTGGGTCGCATAC
ATTAGTAGTGCTAGTGGTCTTATCTCTTATGCCGATGCTGTGAGGGGCCG
GTTCACCATCTCCAGAGACAACGCCAAGAACTCACTGTTCCTACAAATGA
ACAATCTCAAGTCTGAGGACACAGCCATGTATTACTGTGCAAGAGATCCT
CCATATAGCGGTCTCTATGCTCTGGATTTCTGGGGTCAAGGGACCCAAGT
CACCGTCTCCTCA Amino acid:
(SEQ ID NO: 1)
EVQLVESGGGLSQPGNSLQLSCEASGFTFSNHDLNWVRQAPGKGLEWVAY
ISSASGLISYADAVRGRFTISRDNAKNSLFLQMNNLKSEDTAMYYCARDP
PYSGLYALDFWGQGTQVTVSS

FW1:
(SEQ ID NO: 3)
EVQLVESGGGLSQPGNSLQLSCEAS

CDR1:
(SEQ ID NO: 4)
GFTFSNHDLN

FW2:
(SEQ ID NO: 5)
WVRQAPGKGLEWVA

CDR2:
(SEQ ID NO: 6)
YISSASGLISYADAVRG

FW3:
(SEQ ID NO: 7)
RFTISRDNAKNSLFLQMNNLKSEDTAMYYCAR

CDR3:
(SEQ ID NO: 8)
DPPYSGLYALDF

FW4:
(SEQ ID NO: 9)
WGQGTQVTVSS

IGHV3-7*03 Clone 1 (88.8% human)
DNA:
(SEQ ID NO: 35)
GAGGTGCAGCTGGTGGAGTCTGGGGGAGGCTTAGTCCAGCCTGGAGGGTC
CCTGAGACTCTCCTGTGAGGCCTCTGGATTCACCTTCAGTAATCATGATT
TGAACTGGGTCCGCCAGGCTCCAGGGAAGGGGCTGGAGTGGGTCGCATAC
ATTAGTAGTGCTAGTGGTCTTATCTCTTATGCCGATGCTGTGAGGGGCCG
GTTCACCATCTCCAGAGACAACGCCAAGAACTCACTGTATCTACAAATGA
ACAGCCTCAGAGCCGAGGACACAGCCGTGTATTACTGTGCAAGAGATCCT
CCATATAGCGGTCTCTATGCTCTGGATTTCTGGGGTCAAGGGACCCAAGT

CACCGTCTCCTCA

Amino acid:
(SEQ ID NO: 17)
EVQLVESGGGLVQPGGSLRLSCEASGFTFSNHDLNWVRQAPGKGLEWVAY
ISSASGLISYADAVRGRFTISRDNAKNSLYLQMNSLRAEDTAVYYCARDP
PYSGLYALDFWGQGTQVTVSS

FW1:
(SEQ ID NO: 18)
EVQLVESGGGLVQPGGSLRLSCEAS

CDR1:
(SEQ ID NO: 4)
GFTFSNHDLN

FW2:
(SEQ ID NO: 19)
WVRQAPGKGLEWVA

CDR2:
(SEQ ID NO: 6)
YISSASGLISYADAVRG

FW3:
(SEQ ID NO: 20)
RFTISRDNAKNSLYLQMNSLRAEDTAVYYCAR

CDR3:
(SEQ ID NO: 8)
DPPYSGLYALDF

FW4:
(SEQ ID NO: 9)
WGQGTQVTVSS

IGHV3-7*03 Clone 2 (87.8% human)
DNA:
(SEQ ID NO: 36)
GAGGTGCAGCTGGTGGAGTCTGGGGGAGGCTTAGTCCAGCCTGGAGGGTC
CCTGAGACTCTCCTGTGCAGCCTCTGGATTCACCTTCAGTAATCATGATT
TGAACTGGGTCCGCCAGGCTCCAGGGAAGGGGCTGGAGTGGGTCGCATAC
ATTAGTAGTGCTAGTGGTCTTATCTCTTATGCCGATGCTGTGAGGGGCCG
GTTCACCATCTCCAGAGACAACGCCAAGAACTCACTGTATCTACAAATGA
ACAGCCTCAGAGCCGAGGACACAGCCGTGTATTACTGTGCAAGAGATCCT
CCATATAGCGGTCTCTATGCTCTGGATTTCTGGGGTCAAGGGACCCAAGT
CACCGTCTCCTCA Amino acid:
(SEQ ID NO: 21)
EVQLVESGGGLVQPGGSLRLSCAASGFTFSNHDLNWVRQAPGKGLEWVAY
ISSASGLISYADAVRGRFTISRDNAKNSLYLQMNSLRAEDTAVYYCARDP
PYSGLYALDFWGQGTQVTVSS

FW1:
(SEQ ID NO: 22)
EVQLVESGGGLVQPGGSLRLSCAAS

CDR1:
(SEQ ID NO: 4)
GFTFSNHDLN

FW2:
(SEQ ID NO: 19)
WVRQAPGKGLEWVA

CDR2:
(SEQ ID NO: 6)
YISSASGLISYADAVRG

FW3:
(SEQ ID NO: 20)
RFTISRDNAKNSLYLQMNSLRAEDTAVYYCAR

CDR3:
(SEQ ID NO: 8)
DPPYSGLYALDF

FW4:
(SEQ ID NO: 9)
WGQGTQVTVSS

IGHV3-48*03 Clone 1 (85.7% human)
DNA:
(SEQ ID NO: 37)
GAGGTGCAGCTGGTGGAGTCTGGGGGAGGCTTAGTCCAGCCTGGAGGGTC
CCTGAGACTCTCCTGTGAGGCCTCTGGATTCACCTTCAGTAATCATGATT
TGAACTGGGTCCGCCAGGCTCCAGGGAAGGGGCTGGAGTGGGTCTCATAC
ATTAGTAGTGCTAGTGGTCTTATCTCTTATGCCGATGCTGTGAGGGGCCG
GTTCACCATCTCCAGAGACAACGCCAAGAACTCACTGTATCTACAAATGA
ACAGCCTCAGAGCCGAGGACACAGCCGTGTATTACTGTGCAAGAGATCCT
CCATATAGCGGTCTCTATGCTCTGGATTTCTGGGGTCAAGGGACCCAAGT
CACCGTCTCCTCA Amino acid:
(SEQ ID NO: 23)
EVQLVESGGGLVQPGGSLRLSCEASGFTFSNHDLNWVRQAPGKGLEWVSY
ISSASGLISYADAVRGRFTISRDNAKNSLYLQMNSLRAEDTAVYYCARDP
PYSGLYALDFWGQGTQVTVSS

FW1:
(SEQ ID NO: 18)
EVQLVESGGGLVQPGGSLRLSCEAS

CDR1:
(SEQ ID NO: 4)
GFTFSNHDLN

FW2:
(SEQ ID NO: 24)
WVRQAPGKGLEWVS

CDR2:
(SEQ ID NO: 6)
YISSASGLISYADAVRG

FW3:
(SEQ ID NO: 42)
RFTISRDNAKNSLYLQMNSLRAEDTAVYYCAR

CDR3:
(SEQ ID NO: 8)
DPPYSGLYALDF

FW4:
(SEQ ID NO: 9)
WGQGTQVTVSS

IGHV3-48*03 Clone 2 (84.7% human)
DNA:
(SEQ ID NO: 38)
GAGGTGCAGCTGGTGGAGTCTGGGGGAGGCTTAGTCCAGCCTGGAGGGTC
CCTGAGACTCTCCTGTGCAGCCTCTGGATTCACCTTCAGTAATCATGATT
TGAACTGGGTCCGCCAGGCTCCAGGGAAGGGGCTGGAGTGGGTCTCATAC
ATTAGTAGTGCTAGTGGTCTTATCTCTTATGCCGATGCTGTGAGGGGCCG
GTTCACCATCTCCAGAGACAACGCCAAGAACTCACTGTATCTACAAATGA

ACAGCCTCAGAGCCGAGGACACAGCCGTGTATTACTGTGCAAGAGATCCT

CCATATAGCGGTCTCTATGCTCTGGATTTCTGGGGTCAAGGGACCCAAGT

CACCGTCTCCTCA

Amino acid:
(SEQ ID NO: 25)
EVQLVESGGGLVQPGGSLRLSCAASGFTFSNHDLNWVRQAPGKGLEWVSY

ISSASGLISYADAVRGRFTISRDNAKNSLYLQMNSLRAEDTAVYYCARDP

PYSGLYALDFWGQGTQVTVSS

FW1:
(SEQ ID NO: 22)
EVQLVESGGGLVQPGGSLRLSCAAS

CDR1:
(SEQ ID NO: 4)
GFTFSNHDLN

FW2:
(SEQ ID NO: 24)
WVRQAPGKGLEWVS

CDR2:
(SEQ ID NO: 6)
YISSASGLISYADAVRG

FW3:
(SEQ ID NO: 42)
RFTISRDNAKNSLYLQMNSLRAEDTAVYYCAR

CDR3:
(SEQ ID NO: 8)
DPPYSGLYALDF

FW4:
(SEQ ID NO: 9)
WGQGTQVTVSS

Parental clone VL regions (70.6% human)
DNA:
(SEQ ID NO: 39)
CAACCTGTGTTGACTCAGTCACCCTCTGCCTCTGCCTCCCTGAGTGGCTC

AGTCAAACTCACCTGCACCCTGAGTAGTGAACTCAGCTCCTACACCATAG

TATGGTACCAGCAACGTCCAGACAAGGCTCCCAAGTATGTGATGTACCTT

AAGAGTGATGGAAGCCACAGCAAAGGAGATGGGATCCCTGATCGCTTCTC

TGGCTCCAGCTCTGGGGCTCATCGCTACTTAAGCATCTCCAATGTCCAGT

CTGAAGATGATGCTACCTATTTCTGTGGTGCAGGTTATACCCTTGCTGGA

CAATATGGTGGGTGTTCGGTTCAGGCACCAAAGTGACTGTCCTA

Amino acid:
(SEQ ID NO: 2)
QPVLTQSPSASASLSGSVKLTCTLSSELSSYTIVWYQQRPDKAPKYVMYL

KSDGSHSKGDGIPDRFSGSSSGAHRYLSISNVQSEDDATYFCGAGYTLAG

QYGWVFGSGTKVTVL

FW1:
(SEQ ID NO: 10)
QPVLTQSPSASASLSGSVKLTC

CDR1:
(SEQ ID NO: 11)
TLSSELSSYTIV

FW2:
(SEQ ID NO: 12)
WYQQRPDKAPKYVMY

CDR2:
(SEQ ID NO: 13)
LKSDGSHSKGD

FW3:
(SEQ ID NO: 14)
GIPDRFSGSSSGAHRYLSISNVQSEDDATYFC

CDR3:
(SEQ ID NO: 15)
GAGYTLAGQYGWV

FW4:
(SEQ ID NO: 16)
FGSGTKVTVL

IGLV4-60*03 Clone (89.1% human)
DNA:
(SEQ ID NO: 40)
CAACCTGTGTTGACTCAGTCATCCTCTGCCTCTGCCTCCCTGGGATCCTC

AGTCAAACTCACCTGCACCCTGAGTAGTGAACTCAGCTCCTACACCATAG

TATGGCATCAGCAACAGCCAGGGAAGGCTCCCCGGTATTTGATGTACCTT

AAGAGTGATGGAAGCCACAGCAAAGGAGATGGGGTTCCTGATCGCTTCTC

TGGCTCCAGCTCTGGGGCTGACCGCTACTTAACCATCTCCAATCTCCAGT

CTGAAGATGAGGCTGATTATTACTGTGGTGCAGGTTATACCCTTGCTGGA

CAATATGGGTGGGTGTTCGGTTCAGGCACCAAAGTGACTGTCCTA

Amino acid:
(SEQ ID NO: 26)
QPVLTQSSSASASLGSSVKLTCTLSSELSSYTIVWHQQQPGKAPRYLMYL

KSDGSHSKGDGVPDRFSGSSSGADRYLTISNLQSEDEADYYCGAGYTLAG

QYGWVFGSGTKVTVL

FW1:
(SEQ ID NO: 27)
QPVLTQSSSASASLGSSVKLTC

CDR1:
(SEQ ID NO: 11)
TLSSELSSYTIV

FW2:
(SEQ ID NO: 28)
WHQQQPGKAPRYLMY

CDR2:
(SEQ ID NO: 13)
LKSDGSHSKGD

FW3:
(SEQ ID NO: 29)
GVPDRFSGSSSGADRYLTISNLQSEDEADYYC

CDR3:
(SEQ ID NO: 15)
GAGYTLAGQYGWV

FW4:
(SEQ ID NO: 16)
FGSGTKVTVL

IGLV4-69*01 Clone (94.6% human)
DNA:
(SEQ ID NO: 41)
CAACTTGTGTTGACTCAGTCACCCTCTGCCTCTGCCTCCCTGGGAGCCTC

AGTCAAACTCACCTGCACCCTGAGTAGTGAACTCAGCTCCTACACCATAG

TATGGCATCAGCAACAGCCAGAGAAGGGCCCCCGGTATTTGATGTACCTT

AAGAGTGATGGAAGCCACAGCAAAGGAGATGGGATCCCTGATCGCTTCTC

-continued
TGGCTCCAGCTCTGGGGCTGAGCGCTACTTAACCATCTCCAGCCTCCAGT

CTGAAGATGAGGCTGATTATTACTGTGGTGCAGGTTATACCCTTGCTGGA

CAATATGGGTGGGTGTTCGGTTCAGGCACCAAAGTGACTGTCCTA

Amino acid:
                                        (SEQ ID NO: 30)
QLVLTQSPSASASLGASVKLTCTLSSELSSYTIVWHQQQPEKGPRYLMYL

KSDGSHSKGDGIPDRFSGSSSGAERYLTISSLQSEDEADYYCGAGYTLAG

QYGWVFGSGTKVTVL

FW1:
                                        (SEQ ID NO: 31)
QLVLTQSPSASASLGASVKLTC

CDR1:
                                        (SEQ ID NO: 11)
TLSSELSSYTIV

FW2:
                                        (SEQ ID NO: 32)
WHQQQPEKGPRYLMY

CDR2:
                                        (SEQ ID NO: 13)
LKSDGSHSKGD

FW3:
                                        (SEQ ID NO: 33)
GIPDRFSGSSSGAERYLTISSLQSEDEADYYC

CDR3:
                                        (SEQ ID NO: 15)
GAGYTLAGQYGWV

FW4:
                                        (SEQ ID NO: 16)
FGSGTKVTVL

Example 5

In Vitro stimulation of CD4+ and CD8+ T Cell Proliferation by PTX-25

Figure 5:
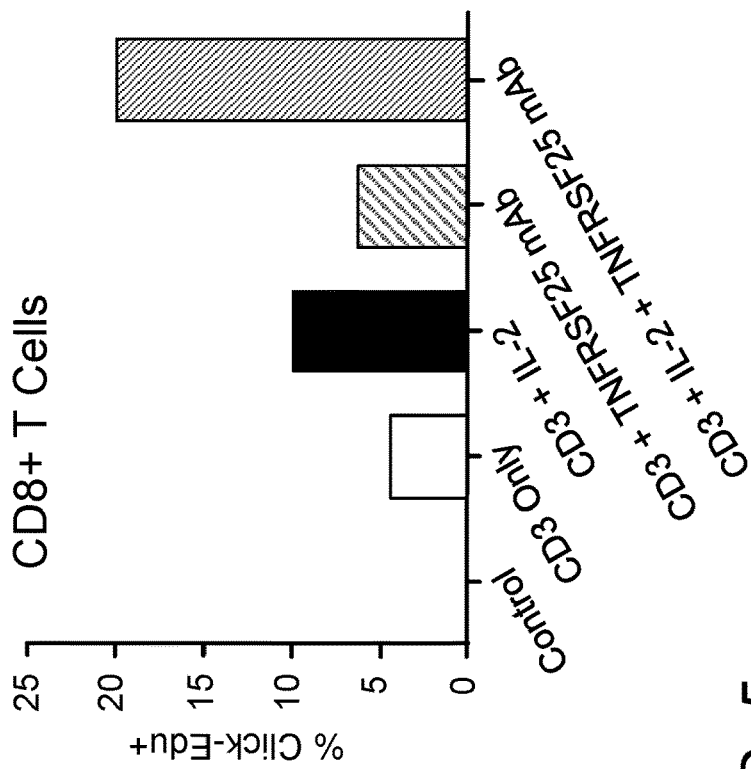
FIG. 5 is a pair of graphs plotting in vitro stimulation of human CD4+ and CD8+ T cell proliferation by PTX-25. Human T cells purified by gradient centrifugation were plated in the presence of plate-bound anti-human CD3 antibody and IL-2, as indicated. PTX-25 was added to the indicated conditions, and proliferation of human CD4+ (left panel) and CD8+ (right panel) T cells was detected using flow cytometry following incorporation of Click-Edu reagent in vitro.
Figure 5:
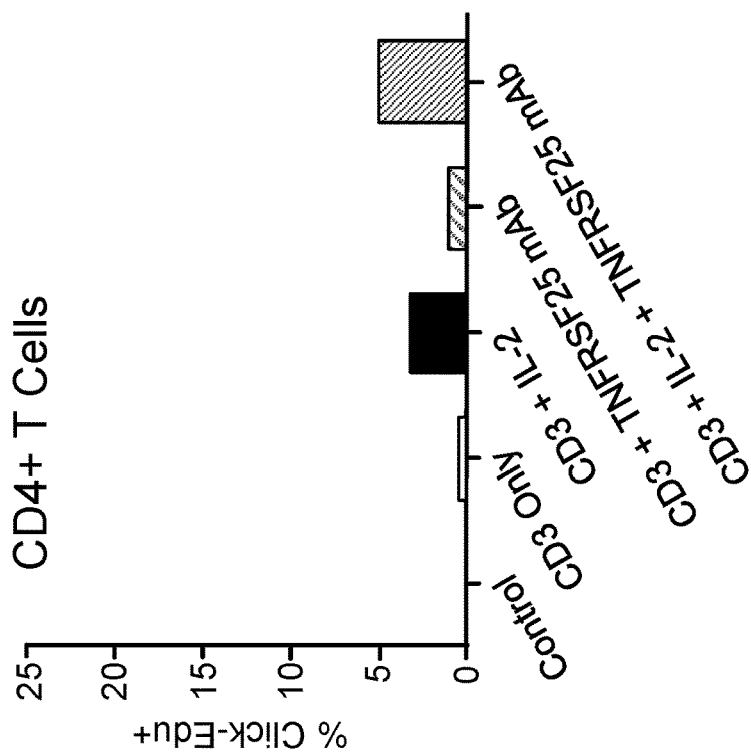

Human T cells were purified by gradient centrifugation and plated in the presence of plate-bound anti-human CD3 antibody and IL-2. PTX-25 was added, and the proliferation of human CD4+ and CD8+ T cells was detected using flow cytometry following incorporation of Click-Edu reagent in vitro. Graphs plotting the in vitro stimulation of human CD4+ and CD8+ T cell proliferation by PTX-25 are shown in FIG. 5. Left panel, CD4+ cells; right panel, CD8+ cells.

Example 6

In Vitro Binding Activity of Humanized TNFRSF25 Antibody Constructs to Human TNFRSF25

The indicated humanized TNFRSF25 antibodies were incubated with P815 cells expressing human TNFRSF25 at the indicated antibody concentrations. Binding of each antibody to the cells was then detected by flow cytometry. The mean fluorescence intensity of binding is indicated on the y-axis for each concentration of antibody indicated on the x-axis (FIG. 6 and TABLE 2).

TABLE 2

|  | Bmax | Kd (μM) |
| --- | --- | --- |
| WBP330BMK1 | 246.0 | 0.07354 |
| WBP330.hAb6.35800 | 255.5 | 0.1014 |
| WBP330.hAb7.35806 | 245.1 | 0.07578 |
| WBP330.hAb2.35816 | 250.4 | 0.08871 |
| WBP330.hAb3.35822 | 242.1 | 0.07678 |
| WBP330.hAb4.35826 | 251.3 | 0.1168 |
| WBP330.hAb8.36811 | 225.9 | 0.07046 |
| WBP330.hAb1.36558 | 238.9 | 0.07299 |

Example 7

Affinity of Humanized TNFRSF25 Antibodies to Human TNFRSF25

Affinity of the indicated humanized TNFRSF25 antibodies was determined by surface plasmon resonance (SPR) using the ProteOn method (FIG. 7 and TABLE 3).

Example 8

In Vitro Caspase Release

Figure 8:
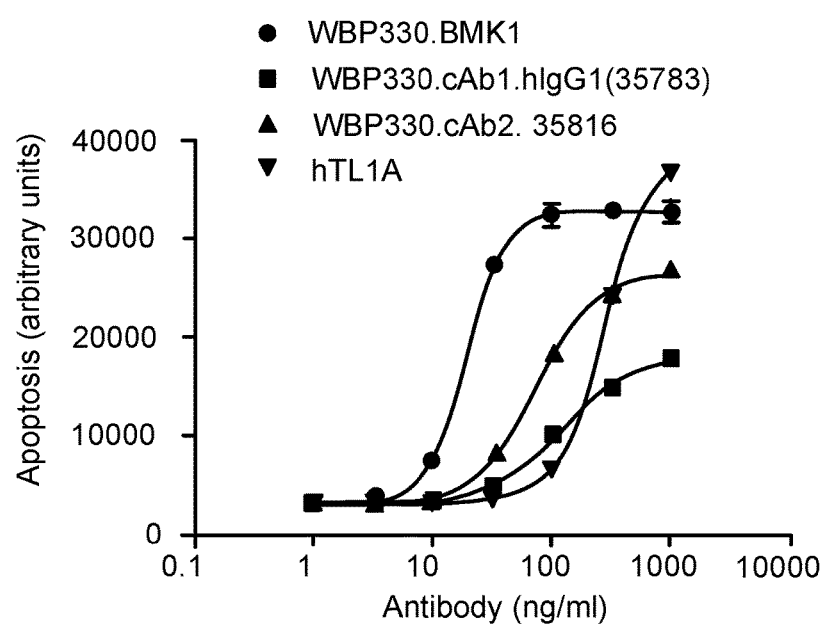
FIG. 8 is a graph plotting functional activity of BMK1, chimeric antibody cAb1.hIgG1 (35783), the most potent humanized antibody (hAb2 (35816)), and an hTL1A-hFc fusion, as determined by detection of caspase activation in vitro.

Caspase release induced by BMK1, chimeric antibody cAb1.hIgG1 (35783), and the most potent humanized antibody hAb2(35816) was tested. Chimeric cAb1.hIgG1 (35783) and humanized hAb2 (35816) induced caspase activities with the $EC_{50}$ of 121.4 and 68.2 ng/ml, respectively, both of which were higher than the $EC_{50}$ of BMK1 (19.2 ng/ml; FIG. 8). The maximal caspase activity induced by the engineered antibodies was significantly lower than by the original 4C12-A5 MAb. The significant difference in in vitro potencies of 4C12-A5 and cAb1.hIgG1 indicated that antibody constant region plays a role in modulating agonistic activity by these antibodies. The in vitro potency of humanized hAb2 was within 3-4 fold of the original hamster MAb. The hTL1A-hFc chimera, which is the ligand for TNFRSF25, induced caspase activity with an $EC_{50}$ of 282.5 ng/ml.

TABLE 3

| | | Bivalent Analyte | | | | | | | |
|---|---|---|---|---|---|---|---|---|---|
| Ligand | Analyte | Ka (1/Ms) | Kd (1/s) | KD (M) | Rmax (RU) | Ka2 (1/RUs) | Kd2 (1/s) | Chi2 (RU) | |
| WBP330.hProl.ECD.hF | WBP330BMK1 | 9.90E+04 | 2.52E-02 | 2.54E-07 | 109.18 | 2.17E-04 | 9.04E-04 | 4.72 | |
| | WBP330.cAB1.hIgG1 (35783) | 9.90E+04 | 5.76E-03 | 5.81E-08 | 83.06 | 3.52E-04 | 2.24E-03 | 5.62 | |
| | WBP330.hAb.35800 | 8.79E+04 | 1.18E-02 | 1.34E-07 | 61.49 | 1.03E-04 | 1.09E-03 | 4.43 | hAb6 |
| | WBP330.hAb.35806 | 8.23E+04 | 1.29E-02 | 1.57E-07 | 57.87 | 1.35E-04 | 1.49E-03 | 4.34 | hAb7 |
| | WBP330.hAb.35816 | 8.90E+04 | 6.32E-03 | 7.09E-08 | 77.57 | 2.38E-04 | 1.28E-03 | 5.07 | hAb2 |
| | WBP335.hAb.35822 | 7.39E+04 | 8.08E-03 | 1.09E-07 | 86.73 | 2.70E-04 | 1.67E-03 | 5.48 | hAb3 |
| | WBP335.hAb.35826 | 7.26E+04 | 1.98E-02 | 2.73E-07 | 107.63 | 2.12E-04 | 1.07E-03 | 6.02 | hAb4 |
| | WBP335.hAb.36811 | 7.13E+04 | 1.49E-02 | 2.08E-07 | 63.40 | 1.52E-04 | 1.68E-03 | 4.53 | hAb8 |
| | WBP330.hAb.36558 | 7.61E+04 | 1.10E-02 | 1.44E-07 | 95.81 | 2.81E-04 | 1.36E-03 | 6.33 | hAb1 |

Example 9

Antibody-Dependent Cell-Mediated Cytotoxicity

Figure 9:
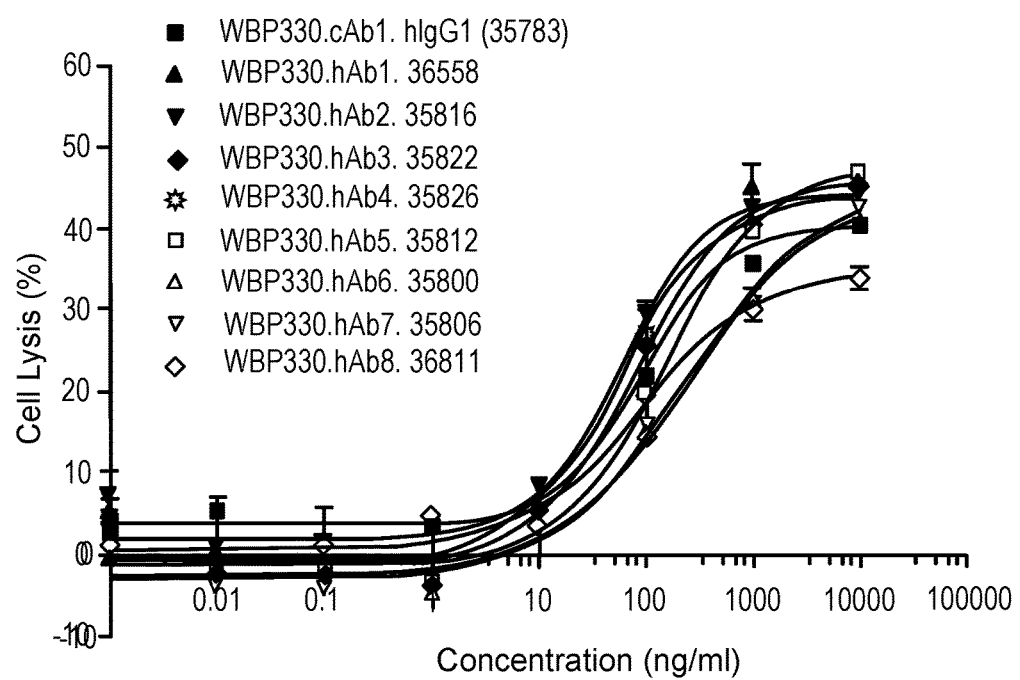
FIG. 9 is a graph plotting antibody-dependent cell-mediated cytotoxicity (ADCC) for the indicated chimeric and humanized antibodies.

The antibody-dependent cell-mediated cytotoxicity (ADCC) of chimeric and humanized antibodies was measured by incubating target cells with PBMCs for 6 hours with an effector/target ratio of 50:1, using indicated IgG concentrations ranging from 10 ug/ml to 0.01 ng/ml. The maximal lysis rate reached 40%, and the $EC_{50}$ for antibodies ranged from 47 ng/ml to 240 ng/ml (FIG. 9; TABLE 4). No significant difference was observed between chimeric and humanized antibodies.

TABLE 4

| | EC50 (ng/ml) | Top % |
|---|---|---|
| cAb1 (35783) | 88.3 | 40.5 |
| hAb1 (36558) | 47.3 | 45.6 |

TABLE 4-continued

| | EC50 (ng/ml) | Top % |
|---|---|---|
| hAb2 (35816) | 56.3 | 44.6 |
| hAb3 (35822) | 79.0 | 46.0 |
| hAb4 (35826) | 60.1 | 44.2 |
| hAb5 (35812) | 148.3 | 47.8 |
| hAb6 (35800) | 199.5 | 43.5 |
| hAb7 (35806) | 239.8 | 45.6 |
| hAb8 (36811) | 85.1 | 34.6 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A humanized monoclonal antibody that specifically binds to TNFRSF25, wherein the antibody comprises:
   (a) a heavy chain comprising a CDR1 sequence as set forth in SEQ ID NO:4, a CDR2 sequence as set forth in SEQ ID NO:6, and a CDR3 sequence as set forth in SEQ ID NO:8; and
   (b) a light chain comprising a CDR1 sequence as set forth in SEQ ID NO:11, a CDR2 sequence as set forth in SEQ ID NO:13, and a CDR3 sequence as set forth in SEQ ID NO:15.

2. The humanized monoclonal antibody of claim 1, wherein the antibody comprises a heavy chain comprising SEQ ID NO: 17, 21, 23, or 25, and a light chain comprising SEQ ID NO: 26 or 30.

3. The humanized antibody of claim 1, wherein the antibody is capable of increasing proliferation of human T cells in vitro or in vivo.

4. The humanized antibody of claim 3, wherein the proliferation of human T cell is increased by at least 20%, as determined by flow cytometry analysis of antigen specific T cells.

5. A pharmaceutical composition comprising a pharmaceutically acceptable carrier and a human or humanized monoclonal antibody that specifically binds to TNFRSF25, wherein the antibody comprises:
   (a) a heavy chain comprising a CDR1 sequence as set forth in SEQ ID NO:4, a CDR2 sequence as set forth in SEQ ID NO:6, and a CDR3 sequence as set forth in SEQ ID NO:8; and
   (b) a light chain comprising a CDR1 sequence as set forth in SEQ ID NO:11, a CDR2 sequence as set forth in SEQ ID NO:13, and a CDR3 sequence as set forth in SEQ ID NO:15.

6. The pharmaceutical composition of claim 5, wherein the antibody comprises a heavy chain comprising the amino acid sequence set forth in SEQ ID NO: 17, 21, 23, or 25, and a light chain comprising the amino acid sequence set forth in SEQ ID NO: 26 or 30.

7. An isolated anti-TNFRSF25 antibody, wherein the antibody comprises:
   (i) a heavy chain variable region sequence comprising the amino acid sequence set forth in SEQ ID NO:1 or the amino acid sequence of SEQ ID NO:1 with no more than 12 total amino acid substitutions; and
   (ii) a light chain variable region sequence comprising the amino acid sequence of SEQ ID NO:2 or the amino acid sequence of SEQ ID NO:2 with no more than 11 total amino acid substitutions.

8. The antibody of claim 7, further comprising a human constant region.

9. The antibody of claim 7, wherein the constant region is selected from the group consisting of human IgG1, IgG2, IgG3, and IgG4.

10. The antibody of claim 7, wherein the constant region is IgG1.

* * * * *

SEQUENCE LISTING

<160> NUMBER OF SEQ ID NOS: 42

<210> SEQ ID NO 1
<211> LENGTH: 121
<212> TYPE: PRT
<213> ORGANISM: Cricetulus migratorius

<400> SEQUENCE: 1

```
Glu Val Gln Leu Val Glu Ser Gly Gly Gly Leu Ser Gln Pro Gly Asn
1               5                   10                  15

Ser Leu Gln Leu Ser Cys Glu Ala Ser Gly Phe Thr Phe Ser Asn His
                20                  25                  30

Asp Leu Asn Trp Val Arg Gln Ala Pro Gly Lys Gly Leu Glu Trp Val
            35                  40                  45

Ala Tyr Ile Ser Ser Ala Ser Gly Leu Ile Ser Tyr Ala Asp Ala Val
        50                  55                  60

Arg Gly Arg Phe Thr Ile Ser Arg Asp Asn Ala Lys Asn Ser Leu Phe
65                  70                  75                  80

Leu Gln Met Asn Asn Leu Lys Ser Glu Asp Thr Ala Met Tyr Tyr Cys
                85                  90                  95

Ala Arg Asp Pro Pro Tyr Ser Gly Leu Tyr Ala Leu Asp Phe Trp Gly
            100                 105                 110

Gln Gly Thr Gln Val Thr Val Ser Ser
        115                 120
```

<210> SEQ ID NO 2
<211> LENGTH: 115
<212> TYPE: PRT
<213> ORGANISM: Cricetulus migratorius

<400> SEQUENCE: 2

```
Gln Pro Val Leu Thr Gln Ser Pro Ala Ser Ala Ser Leu Ser Gly
1               5                   10                  15

Ser Val Lys Leu Thr Cys Thr Leu Ser Glu Leu Ser Ser Tyr Thr
                20                  25                  30

Ile Val Trp Tyr Gln Gln Arg Pro Asp Lys Ala Pro Lys Tyr Val Met
            35                  40                  45

Tyr Leu Lys Ser Asp Gly Ser His Ser Lys Gly Asp Gly Ile Pro Asp
        50                  55                  60

Arg Phe Ser Gly Ser Ser Ser Gly Ala His Arg Tyr Leu Ser Ile Ser
65                  70                  75                  80

Asn Val Gln Ser Glu Asp Asp Ala Thr Tyr Phe Cys Gly Ala Gly Tyr
                85                  90                  95

Thr Leu Ala Gly Gln Tyr Gly Trp Val Phe Gly Ser Gly Thr Lys Val
            100                 105                 110

Thr Val Leu
        115
```

<210> SEQ ID NO 3
<211> LENGTH: 25
<212> TYPE: PRT
<213> ORGANISM: Cricetulus migratorius

<400> SEQUENCE: 3

```
Glu Val Gln Leu Val Glu Ser Gly Gly Gly Leu Ser Gln Pro Gly Asn
1               5                   10                  15

Ser Leu Gln Leu Ser Cys Glu Ala Ser
            20                  25
```

<210> SEQ ID NO 4
<211> LENGTH: 10
<212> TYPE: PRT
<213> ORGANISM: Cricetulus migratorius

<400> SEQUENCE: 4

```
Gly Phe Thr Phe Ser Asn His Asp Leu Asn
1               5                   10
```

<210> SEQ ID NO 5
<211> LENGTH: 14
<212> TYPE: PRT
<213> ORGANISM: Cricetulus migratorius

<400> SEQUENCE: 5

```
Trp Val Arg Gln Ala Pro Gly Lys Gly Leu Glu Trp Val Ala
1               5                   10
```

<210> SEQ ID NO 6
<211> LENGTH: 17
<212> TYPE: PRT
<213> ORGANISM: Cricetulus migratorius

<400> SEQUENCE: 6

```
Tyr Ile Ser Ser Ala Ser Gly Leu Ile Ser Tyr Ala Asp Ala Val Arg
1               5                   10                  15
```

Gly

<210> SEQ ID NO 7
<211> LENGTH: 32
<212> TYPE: PRT
<213> ORGANISM: Cricetulus migratorius

<400> SEQUENCE: 7

Arg Phe Thr Ile Ser Arg Asp Asn Ala Lys Asn Ser Leu Phe Leu Gln
 1               5                  10                  15

Met Asn Asn Leu Lys Ser Glu Asp Thr Ala Met Tyr Tyr Cys Ala Arg
            20                  25                  30

<210> SEQ ID NO 8
<211> LENGTH: 12
<212> TYPE: PRT
<213> ORGANISM: Cricetulus migratorius

<400> SEQUENCE: 8

Asp Pro Pro Tyr Ser Gly Leu Tyr Ala Leu Asp Phe
 1               5                  10

<210> SEQ ID NO 9
<211> LENGTH: 11
<212> TYPE: PRT
<213> ORGANISM: Cricetulus migratorius

<400> SEQUENCE: 9

Trp Gly Gln Gly Thr Gln Val Thr Val Ser Ser
 1               5                  10

<210> SEQ ID NO 10
<211> LENGTH: 22
<212> TYPE: PRT
<213> ORGANISM: Cricetulus migratorius

<400> SEQUENCE: 10

Gln Pro Val Leu Thr Gln Ser Pro Ser Ala Ser Ala Ser Leu Ser Gly
 1               5                  10                  15

Ser Val Lys Leu Thr Cys
            20

<210> SEQ ID NO 11
<211> LENGTH: 12
<212> TYPE: PRT
<213> ORGANISM: Cricetulus migratorius

<400> SEQUENCE: 11

Thr Leu Ser Ser Glu Leu Ser Ser Tyr Thr Ile Val
 1               5                  10

<210> SEQ ID NO 12
<211> LENGTH: 15
<212> TYPE: PRT
<213> ORGANISM: Cricetulus migratorius

<400> SEQUENCE: 12

Trp Tyr Gln Gln Arg Pro Asp Lys Ala Pro Lys Tyr Val Met Tyr
 1               5                  10                  15

<210> SEQ ID NO 13
<211> LENGTH: 11
<212> TYPE: PRT

-continued

<213> ORGANISM: Cricetulus migratorius

<400> SEQUENCE: 13

Leu Lys Ser Asp Gly Ser His Ser Lys Gly Asp
1               5                   10

<210> SEQ ID NO 14
<211> LENGTH: 32
<212> TYPE: PRT
<213> ORGANISM: Cricetulus migratorius

<400> SEQUENCE: 14

Gly Ile Pro Asp Arg Phe Ser Gly Ser Ser Gly Ala His Arg Tyr
1               5                   10                  15

Leu Ser Ile Ser Asn Val Gln Ser Glu Asp Asp Ala Thr Tyr Phe Cys
            20                  25                  30

<210> SEQ ID NO 15
<211> LENGTH: 13
<212> TYPE: PRT
<213> ORGANISM: Cricetulus migratorius

<400> SEQUENCE: 15

Gly Ala Gly Tyr Thr Leu Ala Gly Gln Tyr Gly Trp Val
1               5                   10

<210> SEQ ID NO 16
<211> LENGTH: 10
<212> TYPE: PRT
<213> ORGANISM: Cricetulus migratorius

<400> SEQUENCE: 16

Phe Gly Ser Gly Thr Lys Val Thr Val Leu
1               5                   10

<210> SEQ ID NO 17
<211> LENGTH: 121
<212> TYPE: PRT
<213> ORGANISM: Artificial Sequence
<220> FEATURE:
<223> OTHER INFORMATION: synthetic

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Phe Ser Asn His
            20                  25                  30

Asp Leu Asn Trp Val Arg Gln Ala Pro Gly Lys Gly Leu Glu Trp Val
        35                  40                  45

Ala Tyr Ile Ser Ser Ala Ser Gly Leu Ile Ser Tyr Ala Asp Ala Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Pro Tyr Ser Gly Leu Tyr Ala Leu Asp Phe Trp Gly
            100                 105                 110

Gln Gly Thr Gln Val Thr Val Ser Ser
        115                 120

<210> SEQ ID NO 18

<211> LENGTH: 25
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Glu Ala Ser
            20                  25

<210> SEQ ID NO 19
<211> LENGTH: 14
<212> TYPE: PRT
<213> ORGANISM: Artificial Sequence
<220> FEATURE:
<223> OTHER INFORMATION: synthetic

<400> SEQUENCE: 19

Trp Val Arg Gln Ala Pro Gly Lys Gly Leu Glu Trp Val Ala
1               5                   10

<210> SEQ ID NO 20
<211> LENGTH: 32
<212> TYPE: PRT
<213> ORGANISM: Artificial Sequence
<220> FEATURE:
<223> OTHER INFORMATION: synthetic

<400> SEQUENCE: 20

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 21
<211> LENGTH: 121
<212> TYPE: PRT
<213> ORGANISM: Artificial Sequence
<220> FEATURE:
<223> OTHER INFORMATION: synthetic

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Asp Leu Asn Trp Val Arg Gln Ala Pro Gly Lys Gly Leu Glu Trp Val
        35                  40                  45

Ala Tyr Ile Ser Ser Ala Ser Gly Leu Ile Ser Tyr Ala Asp Ala Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Pro Tyr Ser Gly Leu Tyr Ala Leu Asp Phe Trp Gly
            100                 105                 110

Gln Gly Thr Gln Val Thr Val Ser Ser
        115                 120

<210> SEQ ID NO 22

```
<211> LENGTH: 25
<212> TYPE: PRT
<213> ORGANISM: Artificial Sequence
<220> FEATURE:
<223> OTHER INFORMATION: synthetic

<400> SEQUENCE: 22

Glu Val Gln Leu Val Glu Ser Gly Gly Gly Leu Val Gln Pro Gly Gly
 1               5                  10                  15

Ser Leu Arg Leu Ser Cys Ala Ala Ser
            20                  25

<210> SEQ ID NO 23
<211> LENGTH: 121
<212> TYPE: PRT
<213> ORGANISM: Artificial Sequence
<220> FEATURE:
<223> OTHER INFORMATION: synthetic

<400> SEQUENCE: 23

Glu Val Gln Leu Val Glu Ser Gly Gly Gly Leu Val Gln Pro Gly Gly
 1               5                  10                  15

Ser Leu Arg Leu Ser Cys Glu Ala Ser Gly Phe Thr Phe Ser Asn His
            20                  25                  30

Asp Leu Asn Trp Val Arg Gln Ala Pro Gly Lys Gly Leu Glu Trp Val
        35                  40                  45

Ser Tyr Ile Ser Ser Ala Ser Gly Leu Ile Ser Tyr Ala Asp Ala Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Pro Tyr Ser Gly Leu Tyr Ala Leu Asp Phe Trp Gly
            100                 105                 110

Gln Gly Thr Gln Val Thr Val Ser Ser
        115                 120

<210> SEQ ID NO 24
<211> LENGTH: 14
<212> TYPE: PRT
<213> ORGANISM: Artificial Sequence
<220> FEATURE:
<223> OTHER INFORMATION: synthetic

<400> SEQUENCE: 24

Trp Val Arg Gln Ala Pro Gly Lys Gly Leu Glu Trp Val Ser
 1               5                  10

<210> SEQ ID NO 25
<211> LENGTH: 121
<212> TYPE: PRT
<213> ORGANISM: Artificial Sequence
<220> FEATURE:
<223> OTHER INFORMATION: synthetic

<400> SEQUENCE: 25

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn His
            20                  25                  30

Asp Leu Asn Trp Val Arg Gln Ala Pro Gly Lys Gly Leu Glu Trp Val
        35                  40                  45
```

```
Ser Tyr Ile Ser Ser Ala Ser Gly Leu Ile Ser Tyr Ala Asp Ala Val
    50                  55                  60

Arg Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Asp Pro Pro Tyr Ser Gly Leu Tyr Ala Leu Asp Phe Trp Gly
                100                 105                 110

Gln Gly Thr Gln Val Thr Val Ser Ser
            115                 120

<210> SEQ ID NO 26
<211> LENGTH: 115
<212> TYPE: PRT
<213> ORGANISM: Artificial Sequence
<220> FEATURE:
<223> OTHER INFORMATION: synthetic

<400> SEQUENCE: 26

Gln Pro Val Leu Thr Gln Ser Ser Ala Ser Ala Ser Leu Gly Ser
 1               5                  10                  15

Ser Val Lys Leu Thr Cys Thr Leu Ser Ser Glu Leu Ser Ser Tyr Thr
                20                  25                  30

Ile Val Trp His Gln Gln Pro Gly Lys Ala Pro Arg Tyr Leu Met
                35                  40                  45

Tyr Leu Lys Ser Asp Gly Ser His Ser Lys Gly Asp Gly Val Pro Asp
    50                  55                  60

Arg Phe Ser Gly Ser Ser Gly Ala Asp Arg Tyr Leu Thr Ile Ser
 65                  70                  75                  80

Asn Leu Gln Ser Glu Asp Glu Ala Asp Tyr Tyr Cys Gly Ala Gly Tyr
                85                  90                  95

Thr Leu Ala Gly Gln Tyr Gly Trp Val Phe Gly Ser Gly Thr Lys Val
                100                 105                 110

Thr Val Leu
        115

<210> SEQ ID NO 27
<211> LENGTH: 22
<212> TYPE: PRT
<213> ORGANISM: Artificial Sequence
<220> FEATURE:
<223> OTHER INFORMATION: synthetic

<400> SEQUENCE: 27

Gln Pro Val Leu Thr Gln Ser Ser Ala Ser Ala Ser Leu Gly Ser
 1               5                  10                  15

Ser Val Lys Leu Thr Cys
                20

<210> SEQ ID NO 28
<211> LENGTH: 15
<212> TYPE: PRT
<213> ORGANISM: Artificial Sequence
<220> FEATURE:
<223> OTHER INFORMATION: synthetic

<400> SEQUENCE: 28

Trp His Gln Gln Gln Pro Gly Lys Ala Pro Arg Tyr Leu Met Tyr
 1               5                  10                  15
```

<210> SEQ ID NO 29
<211> LENGTH: 32
<212> TYPE: PRT
<213> ORGANISM: Artificial Sequence
<220> FEATURE:
<223> OTHER INFORMATION: synthetic

<400> SEQUENCE: 29

Gly Val Pro Asp Arg Phe Ser Gly Ser Ser Gly Ala Asp Arg Tyr
1               5                   10                  15

Leu Thr Ile Ser Asn Leu Gln Ser Glu Asp Glu Ala Asp Tyr Tyr Cys
            20                  25                  30

<210> SEQ ID NO 30
<211> LENGTH: 115
<212> TYPE: PRT
<213> ORGANISM: Artificial Sequence
<220> FEATURE:
<223> OTHER INFORMATION: synthetic

<400> SEQUENCE: 30

Gln Leu Val Leu Thr Gln Ser Pro Ser Ala Ser Ala Ser Leu Gly Ala
1               5                   10                  15

Ser Val Lys Leu Thr Cys Thr Leu Ser Ser Glu Leu Ser Ser Tyr Thr
            20                  25                  30

Ile Val Trp His Gln Gln Pro Glu Lys Gly Pro Arg Tyr Leu Met
        35                  40                  45

Tyr Leu Lys Ser Asp Gly Ser His Ser Lys Gly Asp Gly Ile Pro Asp
    50                  55                  60

Arg Phe Ser Gly Ser Ser Gly Ala Glu Arg Tyr Leu Thr Ile Ser
65                  70                  75                  80

Ser Leu Gln Ser Glu Asp Glu Ala Asp Tyr Tyr Cys Gly Ala Gly Tyr
                85                  90                  95

Thr Leu Ala Gly Gln Tyr Gly Trp Val Phe Gly Ser Gly Thr Lys Val
            100                 105                 110

Thr Val Leu
    115

<210> SEQ ID NO 31
<211> LENGTH: 22
<212> TYPE: PRT
<213> ORGANISM: Artificial Sequence
<220> FEATURE:
<223> OTHER INFORMATION: synthetic

<400> SEQUENCE: 31

Gln Leu Val Leu Thr Gln Ser Pro Ser Ala Ser Ala Ser Leu Gly Ala
1               5                   10                  15

Ser Val Lys Leu Thr Cys
            20

<210> SEQ ID NO 32
<211> LENGTH: 15
<212> TYPE: PRT
<213> ORGANISM: Artificial Sequence
<220> FEATURE:
<223> OTHER INFORMATION: synthetic

<400> SEQUENCE: 32

Trp His Gln Gln Gln Pro Glu Lys Gly Pro Arg Tyr Leu Met Tyr
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: synthetic

<400> SEQUENCE: 33

Gly Ile Pro Asp Arg Phe Ser Gly Ser Ser Gly Ala Glu Arg Tyr
1               5                   10                  15
Leu Thr Ile Ser Ser Leu Gln Ser Glu Asp Glu Ala Asp Tyr Tyr Cys
            20                  25                  30

<210> SEQ ID NO 34
<211> LENGTH: 363
<212> TYPE: DNA
<213> ORGANISM: Cricetulus migratorius

<400> SEQUENCE: 34
gaggtgcagc tggtggagtc tgggggaggc ttatcacagc ctggaaattc cctgcaactc      60
tcctgtgagg cctctggatt caccttcagt aatcatgatt tgaactgggt ccgccaggct     120
ccagggaagg gctggagtg gtcgcatac attagtagtg ctagtggtct tatctcttat      180
gccgatgctg tgaggggccg gttcaccatc tccagagaca acgccaagaa ctcactgttc     240
ctacaaatga acaatctcaa gtctgaggac acagccatgt attactgtgc aagagatcct     300
ccatatagcg gtctctatgc tctggatttc tggggtcaag gacccaagt caccgtctcc      360 tca                                                                  363

<210> SEQ ID NO 35
<211> LENGTH: 363
<212> TYPE: DNA
<213> ORGANISM: Artificial Sequence
<220> FEATURE:
<223> OTHER INFORMATION: synthetic

<400> SEQUENCE: 35
gaggtgcagc tggtggagtc tgggggaggc ttagtccagc ctggagggtc cctgagactc      60
tcctgtgagg cctctggatt caccttcagt aatcatgatt tgaactgggt ccgccaggct     120
ccagggaagg gctggagtg gtcgcatac attagtagtg ctagtggtct tatctcttat      180
gccgatgctg tgaggggccg gttcaccatc tccagagaca acgccaagaa ctcactgtat     240
ctacaaatga acagcctcag agccgaggac acagccgtgt attactgtgc aagagatcct     300
ccatatagcg gtctctatgc tctggatttc tggggtcaag gacccaagt caccgtctcc      360 tca                                                                  363

<210> SEQ ID NO 36
<211> LENGTH: 363
<212> TYPE: DNA
<213> ORGANISM: Artificial Sequence
<220> FEATURE:
<223> OTHER INFORMATION: synthetic

<400> SEQUENCE: 36
gaggtgcagc tggtggagtc tgggggaggc ttagtccagc ctggagggtc cctgagactc      60
tcctgtgcag cctctggatt caccttcagt aatcatgatt tgaactgggt ccgccaggct     120
ccagggaagg gctggagtg gtcgcatac attagtagtg ctagtggtct tatctcttat      180
gccgatgctg tgaggggccg gttcaccatc tccagagaca acgccaagaa ctcactgtat     240

```
ctacaaatga acagcctcag agccgaggac acagccgtgt attactgtgc aagagatcct    300
ccatatagcg gtctctatgc tctggatttc tggggtcaag ggacccaagt caccgtctcc    360
tca                                                                  363

<210> SEQ ID NO 37
<211> LENGTH: 363
<212> TYPE: DNA
<213> ORGANISM: Artificial Sequence
<220> FEATURE:
<223> OTHER INFORMATION: synthetic

<400> SEQUENCE: 37
gaggtgcagc tggtggagtc tgggggaggc ttagtccagc ctggagggtc cctgagactc    60
tcctgtgagg cctctggatt caccttcagt aatcatgatt tgaactgggt ccgccaggct    120
ccagggaagg ggctggagtg ggtctcatac attagtagtg ctagtggtct tatctcttat    180
gccgatgctg tgaggggccg gttcaccatc tccagagaca acgccaagaa ctcactgtat    240
ctacaaatga acagcctcag agccgaggac acagccgtgt attactgtgc aagagatcct    300
ccatatagcg gtctctatgc tctggatttc tggggtcaag ggacccaagt caccgtctcc    360
tca                                                                  363

<210> SEQ ID NO 38
<211> LENGTH: 363
<212> TYPE: DNA
<213> ORGANISM: Artificial Sequence
<220> FEATURE:
<223> OTHER INFORMATION: synthetic

<400> SEQUENCE: 38
gaggtgcagc tggtggagtc tgggggaggc ttagtccagc ctggagggtc cctgagactc    60
tcctgtgcag cctctggatt caccttcagt aatcatgatt tgaactgggt ccgccaggct    120
ccagggaagg ggctggagtg ggtctcatac attagtagtg ctagtggtct tatctcttat    180
gccgatgctg tgaggggccg gttcaccatc tccagagaca acgccaagaa ctcactgtat    240
ctacaaatga acagcctcag agccgaggac acagccgtgt attactgtgc aagagatcct    300
ccatatagcg gtctctatgc tctggatttc tggggtcaag ggacccaagt caccgtctcc    360
tca                                                                  363

<210> SEQ ID NO 39
<211> LENGTH: 345
<212> TYPE: DNA
<213> ORGANISM: Cricetulus migratorius

<400> SEQUENCE: 39
caacctgtgt tgactcagtc accctctgcc tctgcctccc tgagtggctc agtcaaactc    60
acctgcaccc tgagtagtga actcagctcc tacaccatag tatggtacca gcaacgtcca    120
gacaaggctc ccaagtatgt gatgtacctt aagagtgatg aagccacagc aaaggagat    180 gggatccctg atcgcttctc tggctccagc tctgggctc atcgctactt aagcatctcc    240
aatgtccagt ctgaagatga tgctacctat ttctgtggtg caggttatac ccttgctgga    300
caatatgggt gggtgttcgg ttcaggcacc aaagtgactg tccta                    345

<210> SEQ ID NO 40
<211> LENGTH: 345
<212> TYPE: DNA
```

```
<213> ORGANISM: Artificial Sequence
<220> FEATURE:
<223> OTHER INFORMATION: synthetic

<400> SEQUENCE: 40
caacctgtgt tgactcagtc atcctctgcc tctgcctccc tgggatcctc agtcaaactc      60
acctgcaccc tgagtagtga actcagctcc tacaccatag tatggcatca gcaacagcca     120
gggaaggctc cccggtattt gatgtaccct aagagtgatg gaagccacag caaaggagat     180
ggggttcctg atcgcttctc tggctccagc tctggggctg accgctactt aaccatctcc     240
aatctccagt ctgaagatga ggctgattat tactgtggtg caggttatac ccttgctgga     300
caatatgggg ggtgttcgg ttcaggcacc aaagtgactg tccta                      345

<210> SEQ ID NO 41
<211> LENGTH: 345
<212> TYPE: DNA
<213> ORGANISM: Artificial Sequence
<220> FEATURE:
<223> OTHER INFORMATION: synthetic

<400> SEQUENCE: 41
caacttgtgt tgactcagtc accctctgcc tctgcctccc tgggagcctc agtcaaactc      60
acctgcaccc tgagtagtga actcagctcc tacaccatag tatggcatca gcaacagcca     120
gagaagggcc cccggtattt gatgtaccct aagagtgatg gaagccacag caaaggagat     180
gggatccctg atcgcttctc tggctccagc tctggggctg agcgctactt aaccatctcc     240
agcctccagt ctgaagatga ggctgattat tactgtggtg caggttatac ccttgctgga     300
caatatgggt gggtgttcgg ttcaggcacc aaagtgactg tccta                     345

<210> SEQ ID NO 42
<211> LENGTH: 32
<212> TYPE: PRT
<213> ORGANISM: Artificial Sequence
<220> FEATURE:
<223> OTHER INFORMATION: synthetic

<400> SEQUENCE: 42

Arg Phe Thr Ile Ser Arg Asp Asn Ala Lys Asn Ser Leu Tyr Leu Gln
 1               5                  10                  15

Met Asn Ser Leu Arg Ala Glu Asp Thr Ala Val Tyr Tyr Cys Ala Arg
            20                  25                  30
```